US009922268B2

United States Patent
Iwamura et al.

(10) Patent No.: US 9,922,268 B2
(45) Date of Patent: Mar. 20, 2018

(54) IMAGE INTERPRETATION REPORT CREATING APPARATUS AND IMAGE INTERPRETATION REPORT CREATING SYSTEM

(71) Applicant: TOSHIBA MEDICAL SYSTEMS CORPORATION, Otawara-Shi (JP)

(72) Inventors: Taisuke Iwamura, Nasushiobara (JP); Kousuke Sakaue, Nasushiobara (JP); Masashi Yoshida, Nasushiobara (JP); Shigeyuki Ishii, Nasushiobara (JP); Satoshi Ikeda, Yaita (JP); Hitoshi Yamagata, Otawara (JP); Takashi Masuzawa, Otawara (JP); Naoki Sugiyama, Otawara (JP); Muneyasu Kazuno, Nasushiobara (JP); Yosuke Okubo, Nasushiobara (JP); Hiroyuki Yamasaki, Yaita (JP); Jun Kawakami, Otawara (JP); Takashi Kondo, Otawara (JP); Guang Yi Ong, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 125 days.

(21) Appl. No.: 14/638,589

(22) Filed: Mar. 4, 2015

(65) Prior Publication Data
US 2015/0262014 A1 Sep. 17, 2015

(30) Foreign Application Priority Data
Mar. 11, 2014 (JP) ................................. 2014-048082

(51) Int. Cl.
*G06K 9/62* (2006.01)
*G06T 7/70* (2017.01)
*G06F 19/00* (2011.01)

(52) U.S. Cl.
CPC ......... *G06K 9/6253* (2013.01); *G06F 19/321* (2013.01); *G06F 19/345* (2013.01);
(Continued)

(58) Field of Classification Search
CPC ............ G06K 9/6253; G06K 2209/051; G06F 19/345; G06F 19/321; G06T 7/004;
(Continued)

(56) References Cited

U.S. PATENT DOCUMENTS

2008/0215525 A1* 9/2008 Kakimoto ............. G06F 19/321
2009/0132499 A1* 5/2009 Yamagishi .......... G06F 19/3443
(Continued)

FOREIGN PATENT DOCUMENTS

JP 2008-259682 10/2008
JP 2009-69977 4/2009
(Continued)

*Primary Examiner* — Bhavesh Mehta
*Assistant Examiner* — Menatoallah Youssef
(74) *Attorney, Agent, or Firm* — Oblon, McClelland, Maier & Neustadt, L.L.P.

(57) ABSTRACT

According to one embodiment, an image interpretation report creating apparatus that creates an image interpretation report including a finding and is associated with a key image, includes a key image selecting unit, a position detecting unit, a first local structure information generating unit, and a display. A key image selecting unit selects a sub-image as the key image from among a plurality of sub-images comprising a medical image. A position detecting unit detects a position of a characteristic local structure in a human body from the medical image. A first local structure information generating unit identifies a local structure in the key image or in a vicinity of the key image and generates information on the identified local structure as first local structure information. A display displays the first local structure information as a candidate to be entered in an entry field for the finding.

15 Claims, 23 Drawing Sheets

(52) U.S. Cl.
CPC .......... *G06T 7/70* (2017.01); *G06K 2209/051* (2013.01); *G06T 2207/10072* (2013.01); *G06T 2207/30004* (2013.01)

(58) Field of Classification Search
CPC ........... G06T 2207/10072; G06T 2207/30004; G06Q 50/24
See application file for complete search history.

(56) References Cited

U.S. PATENT DOCUMENTS

| | | | | |
|---|---|---|---|---|
| 2011/0182493 | A1* | 7/2011 | Huber | G06F 19/3487 382/132 |
| 2012/0176408 | A1* | 7/2012 | Moriya | A61B 5/0013 345/629 |
| 2012/0321153 | A1* | 12/2012 | Dwivedi | A61B 6/469 382/128 |
| 2015/0261915 | A1* | 9/2015 | Yanagida | G06F 19/321 382/131 |
| 2015/0279061 | A1* | 10/2015 | Kutsuna | G06T 11/003 382/131 |
| 2016/0048987 | A1* | 2/2016 | Sevenster | G06T 11/60 715/232 |

FOREIGN PATENT DOCUMENTS

| | | |
|---|---|---|
| JP | 2010-178842 | 8/2010 |
| JP | 2011-86276 | 4/2011 |
| JP | 5138431 | 2/2013 |
| JP | 5197029 | 5/2013 |

* cited by examiner

FIG. 5A

| HEAD, NECK |
| --- |
| ANTERIOR ARCH (TUBERCLE) OF ATLAS (CERVICAL VERTEBRA I) |
| SUPERIOR TIP OF DENS / PEG (CERVICAL VERTEBRA II) |
| SUPERIOR ASPECT OF RIGHT EYE GLOBE |
| SUPERIOR ASPECT OF LEFT EYE GLOBE |
| CENTER OF RIGHT EYE GLOBE |
| CENTER OF LEFT EYE GLOBE |
| ⋮ |

FIG. 5B

| CHEST |
| --- |
| BIFURCATION OF TRACHEA |
| APEX OF RIGHT LUNG |
| APEX OF LEFT LUNG |
| INFERIOR ANGLE OF RIGHT SCAPULA |
| INFERIOR ANGLE OF LEFT SCAPULA |
| START OF LEFT SUBCLAVIAN ARTERY (BRANCHING OFF AORTIC ARCH) |
| ⋮ |

FIG. 5C

| ABDOMEN |
| --- |
| SUPERIOR POLE OF RIGHT KIDNEY |
| SUPERIOR POLE OF LEFT KIDNEY |
| INFERIOR POLE OF RIGHT KIDNEY |
| INFERIOR POLE OF LEFT KIDNEY |
| HEAD OF PANCREAS |
| TIP OF TAIL OF PANCREAS |
| ⋮ |

FIG. 5D

| LOWER LIMBS |
| --- |
| LATERAL EPICONDYLE OF RIGHT FEMUR |
| MEDIAL EPICONDYLE OF RIGHT FEMUR |
| LATERAL EPICONDYLE OF LEFT FEMUR |
| MEDIAL EPICONDYLE OF LEFT FEMUR |
| LATERAL CONDYLE OF RIGHT TIBIA |
| MEDIAL CONDYLE OF RIGHT TIBIA |
| ⋮ |

| IDENTIFIER | NAME | RELIABILITY | SITE | BODY TISSUE | PATIENT COORDINATE SYSTEM | | |
|---|---|---|---|---|---|---|---|
| | | | | | X | Y | Z |
| ABD025.C | CENTER OF BODY OF L5 | 0.87 | ABDOMEN | SKELETAL SYSTEM | -3.1 | 23.4 | 90.0 |
| ABD032.C | SUPERIOR ASPECT OF RIGHT ILIAC SPINE | 0.82 | ABDOMEN | SKELETAL SYSTEM | -11.1 | -54.4 | 84.1 |
| ABD039.C | SUPERIOR ASPECT OF LEFT ILIAC SPINE | 0.83 | ABDOMEN | SKELETAL SYSTEM | -3.0 | 30.0 | 104.0 |
| ⋮ | ⋮ | ⋮ | ⋮ | ⋮ | ⋮ | ⋮ | ⋮ |

| LOCAL STRUCTURE | COORDINATES | SLICE NUMBER |
|---|---|---|
| AL4 | (X1a, Y1a) | 30 |
| AL5 | (X2a, Y2a) | 32 |
| AL6 | (X3a, Y3a) | 33 |
| AL7 | (X4a, Y4a) | 37 |

| KEY IMAGE LOCAL STRUCTURE LIST | POSITION INFORMATION /40a4 |
|---|---|
| BIFURCATION OF TRACHEA | – |
| APEX OF RIGHT LUNG | AAA cm IN △ DIRECTION |
| APEX OF LEFT LUNG | BBB cm IN ○ DIRECTION |
| INFERIOR ANGLE OF RIGHT SCAPULA | CCC cm IN □ DIRECTION |
| ⋮ | ⋮ |

FIG. 13A

| SELECT | KEY IMAGE LOCAL STRUCTURE LIST | POSITION INFORMATION /40a4 |
|---|---|---|
| ☐ | BIFURCATION OF TRACHEA | – |
| ☑ | APEX OF RIGHT LUNG | AAA cm IN △ DIRECTION |
| ☐ | APEX OF LEFT LUNG | BBB cm IN ○ DIRECTION |
| ☑ | INFERIOR ANGLE OF RIGHT SCAPULA | CCC cm IN □ DIRECTION |
| ⋮ | ⋮ | ⋮ |

FIG. 13B

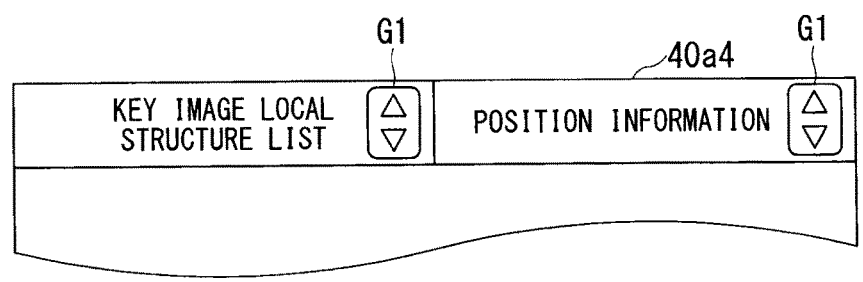

FIG. 13C

| FINDING LOCAL STRUCTURE LIST |
|---|
| APEX OF RIGHT LUNG |
| INFERIOR ANGLE OF RIGHT SCAPULA |
| BIFURCATION OF TRACHEA |
| ⋮ |

| FINDING LOCAL STRUCTURE LIST |
|---|
| MOST INFERIOR ASPECT OF LIVER |
| POSTERIOR ASPECT OF LIVER |
| ORIGIN OF THE HEPATIC ARTERY |
| ⋮ |

| DATE OF REPORT CREATION ◀▶ | PATIENT NAME ◀▶ | STUDY DATE ◀▶ | MODALITY DEVICE ◀▶ | REPRESENTATIVE SITE ◀▶ | DEGREE OF MATCHING ◀▶ B1 |
|---|---|---|---|---|---|
| 2013/05/02 | PATIENT A | 2013/05/02 | CT | CHEST | 0.95 |
| 2013/04/27 | PATIENT B | 2013/04/25 | CT | CHEST | 0.85 |
| 2013/04/16 | PATIENT C | 2013/04/15 | MRI | ABDOMEN | 0.80 |
| ... | ... | ... | ... | ... | ... |

T3

T4
☑ HEAD
☐ CHEST
☐ ABDOMEN
...

NARROW DOWN CRITERION 1  | METASTASIS DESTINATION/COMPLICATION SITE ▶ |  B2

FIG. 20

DEGREE OF MATCHING CALCULATION CRITERION

CRITERION 1 | CLOSEST AL FOR KEY IMAGE ▼

CRITERION 2 | DISTANCE ▼

PRESENCE OR ABSENCE OF MATCHING
NUMBER OF MATCHINGS
PERCENTAGE OF MATCHING
⋮

UPPER LIMIT VALUE OF DEGREE OF MATCHING

0.8   ⦿ EQUAL TO OR GREATER THAN
      ○ EQUAL TO
      ○ GREATER THAN

T5:
- ☑ DISTANCE BETWEEN SLICES
- ☐ DISTANCE BETWEEN POINTS
- ☐ DISTANCE IN X AXIS DIRECTION
- ☐ DISTANCE IN Y AXIS DIRECTION

FIG. 21

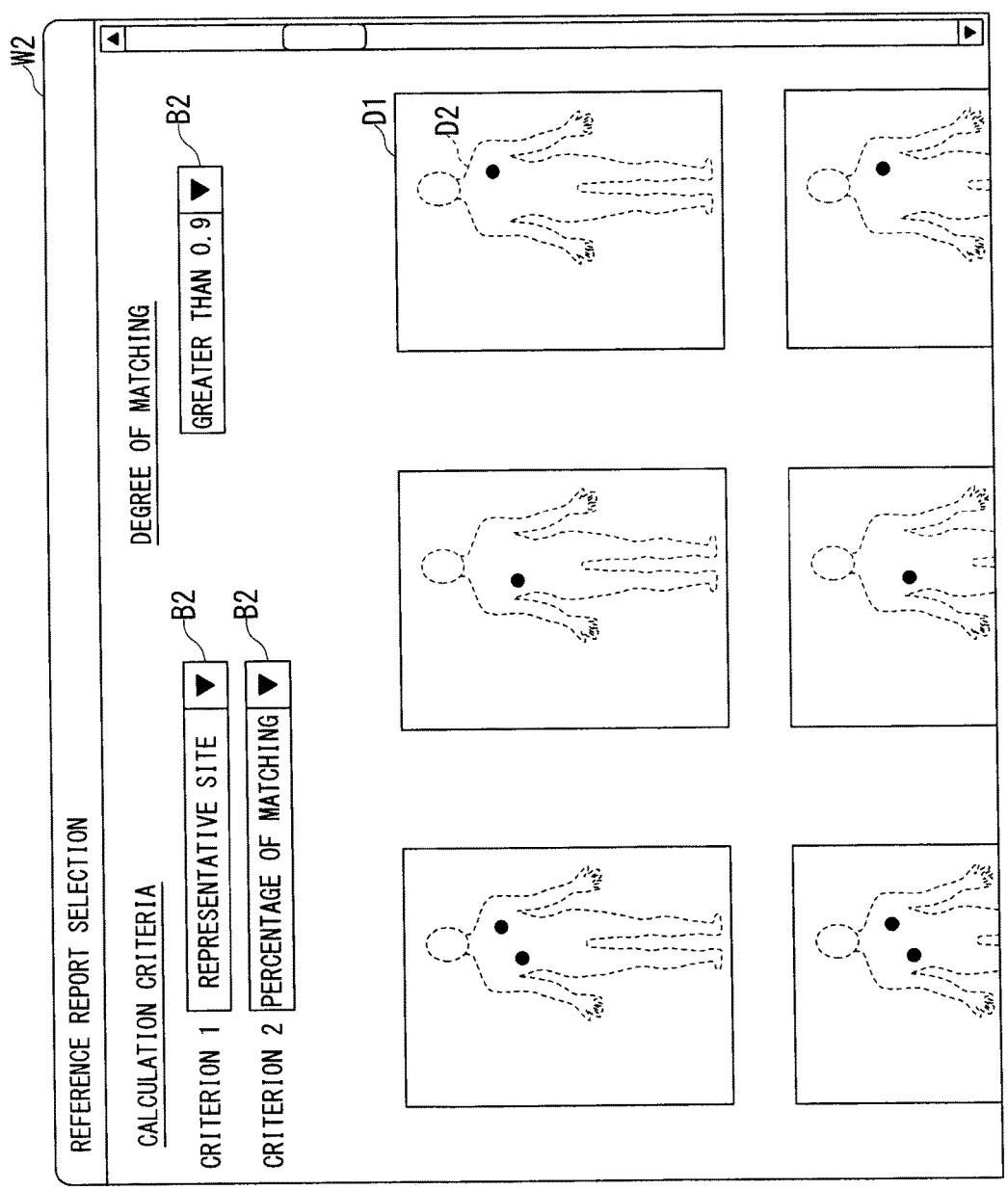

IMAGE INTERPRETATION REPORT CREATING APPARATUS AND IMAGE INTERPRETATION REPORT CREATING SYSTEM

CROSS-REFERENCE TO RELATED APPLICATIONS

This application claims the benefit of priority of Japanese Patent Application No. 2014-048082, filed Mar. 11, 2014, the entire contents of which are incorporated herein by reference.

FIELD

Embodiments described herein relate generally to an image interpretation report creating apparatus and an image interpretation report creating system.

BACKGROUND

Various inspection devices (referred to as modality devices, hereinafter) used in image diagnosis are essential in the modern medicine, because those inspection devices can perform minimally invasive inspection of a human body. Advances in performance of the modality devices have allowed a quality image of high resolution to be obtained and accurate and precise inspection to be achieved in image diagnosis. For example, a computed tomography (CT) apparatus can obtain high-resolution three-dimensional information on a tissue inside an object, and a magnetic resonance imaging (MRI) apparatus can perform imaging in various ways depending on the modality device, such as an MR angiography (MRA) that images fresh blood containing no contrast medium by MRI. With advances in medical image digitalization, a hospital information system (HIS) that is an ordering system that processes a request from a doctor via an electronic network, a radiology information system (RIS) and a picture archiving and communication system (PACS) that accumulates images obtained by the modality device as electronic data have been developed.

Advances of the modality devices have enabled easy and detailed observation of the inside of a living body. An enormous amount of data can be obtained, and many modality devices obtain data in the form of volume data composed of a plurality of images. The amount of volume data is no less than thousands of images when a whole body is imaged, and it is burdensome to a doctor or the like who performs image interpretation of these data to make a diagnosis. Image interpretation is an important task for diagnosis of a disease or determination of a treatment plan. It is not easy to analyze the enormous amount of medical images to make an early decision, although there is a demand for early detection. In view of such circumstances, as inventions for supporting image diagnosis, there have been proposed a medical image processing apparatus that identifies an abnormal anatomical site and determines the degree of malignancy of the site by using a segmentation technique or the like (see Patent Literature 1, for example) and an image analyzing apparatus (see Patent Literature 2, for example) that determines a positional correspondence between images obtained in two different inspections.

Image interpretation and diagnosis need to be accurate, and to make an accurate diagnosis, an abnormal site or a site to be treated in the obtained medical image needs to be precisely grasped. However, to read an anatomical site from a medical image requires technical expertise. In view of this, techniques of representing or constructing an anatomical position in a human body through a mathematical approach have been studied and provided.

The "anatomical position" refers to a characteristic local structure in a human body (referred to as a local structure, hereinafter) that is important for understanding a medical image and serves as a mark when the human body is anatomically mapped. For example, an anterior arch (node) of a first cervical vertebra (cervical vertebra I) of a head is a local structure, a bifurcation of trachea in a chest is also a local structure, and an upper pole of a right kidney or the like in an abdomen is also a local structure. The position of the local structure (anatomical position) is automatically detected from the medical image obtained by the modality device, such as the X-ray CT device or the MRI device, by common image analysis, pattern recognition technique or the like.

A diagnostic reader (e.g. radiologist or the like) creates an image interpretation report based on the result of an image interpretation. In the image interpretation report, the anatomical site of an abnormality found in the image interpretation and the status of the abnormality are recorded as findings. Creation of the image interpretation report requires a task of selecting a representative image (referred to as a key image, hereinafter) that includes a finding and attaching a mark (referred to as an annotation, hereinafter) to the key image at a particular position of interest.

In a medical examination, the reader has to perform such an image interpretation report creation task for hundreds of patients. In some cases, an enormous amount of data containing hundreds or thousands of medical images is obtained per person in one X-ray CT or MRI imaging, and creation of an image interpretation report requires selecting a possible key image from among the enormous amount of medical image data and entering a finding for the selected key image. Such creation of an image interpretation report is a significant burden in image diagnosis.

In view of such circumstances, there is a demand for an image interpretation report creating apparatus that assists creation of an image interpretation report by making a list of a candidate site of a finding from a selected key image based on the position (anatomical position) of the local structure.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5A shows examples of local structures of a head and a neck;

FIG. 5B shows, as local structures of a chest, a bifurcation of trachea, an apex of a right lung, an apex of a left lung, an inferior angle of a right scapula, an inferior angle of a left scapula and an origin of a left subclavian artery;

FIG. 5C shows, as local structures of an abdomen, an upper pole of a right kidney, an upper pole of a left kidney, a lower pole of a right kidney, a lower pole of a left kidney, a head of a pancreas and a tip of a tail of a pancreas;

FIG. 5D shows, as local structures of lower limbs, a lateral epicondyle of a right femur, a medial epicondyle of a right femur, a lateral epicondyle of a left femur, a medial epicondyle of a left femur, a lateral condyle of a right tibia and a medial condyle of a right tibia;

FIG. 13A shows an example in which the list of local structures is displayed with distances calculated by the position information generating unit;

FIG. 13B shows an example in which checkboxes are used for selection of a plurality of local structures;

FIG. 13C shows an example in which sort buttons G1 to select whether to display in ascending order or descending order are provided in item name fields of the list;

FIG. 20 is a diagram for illustrating a first example of a screen for inputting a narrow-down criterion of the image interpretation report creating apparatus 100 according to the third embodiment;

FIG. 21 is a diagram for illustrating a second example of the screen for inputting a narrow-down criterion of the image interpretation report creating apparatus 100 according to the third embodiment;

FIG. 22 is a diagram for illustrating a case of displaying thumbnails of reference reports.

DETAILED DESCRIPTION

Hereinbelow, a description will be given of an image interpretation report creating apparatus and an image interpretation report creating system according to embodiments of the present invention with reference to the drawings.

In general, according to one embodiment, an image interpretation report creating apparatus that creates an image interpretation report including a finding and is associated with a key image, includes a key image selecting unit, a position detecting unit, a first local structure information generating unit, and a display. A key image selecting unit selects a sub-image as the key image from among a plurality of sub-images comprising a medical image. A position detecting unit detects a position of a characteristic local structure in a human body from the medical image. A first local structure information generating unit identifies a local structure in the key image or in a vicinity of the key image and generates information on the identified local structure as first local structure information. A display displays the first local structure information as a candidate to be entered in an entry field for the finding.

(Overall Configuration)

Figure 1:
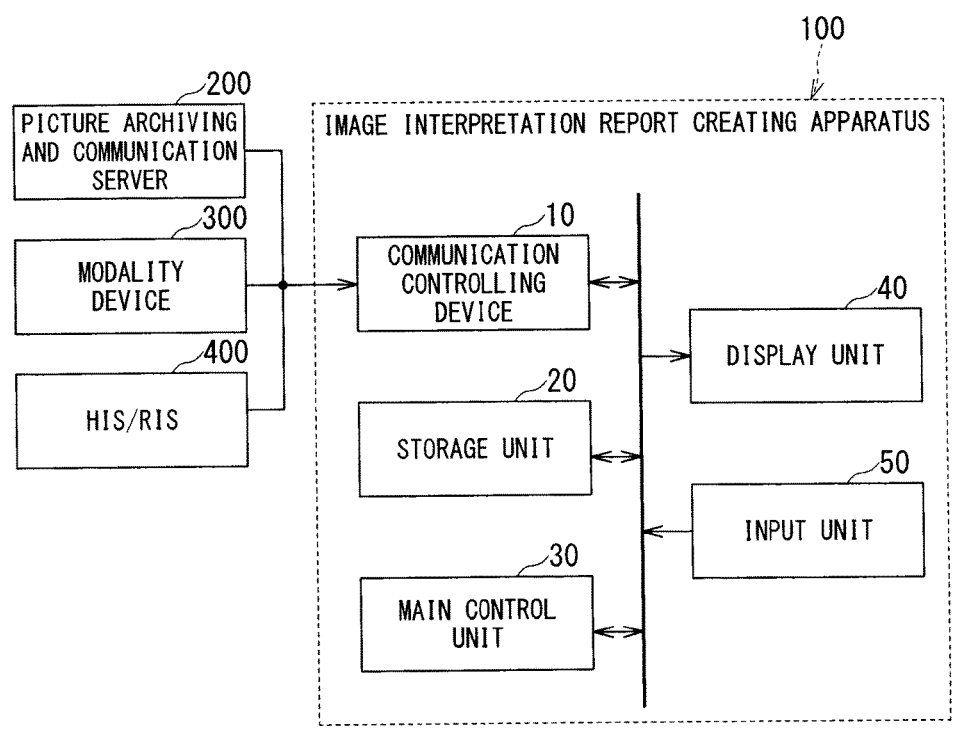
FIG. 1 is a conceptual diagram showing an example of an image interpretation report creating apparatus 100 according to an embodiment.

FIG. 1 is a conceptual diagram showing an example of an image interpretation report creating apparatus 100 according to an embodiment. The image interpretation report creating apparatus 100 according to the embodiment may be implemented as a function of an image processing apparatus including display of the various modalities, or may be implemented as a function of an image analyzing workstation or the like.

As shown in FIG. 1, the image interpretation report creating apparatus 100 comprises a communication controlling device 10, a storage unit 20, a main control unit 30, a display unit 40 and an input unit 50. The image interpretation report creating apparatus 100 is connected to a picture archiving and communication server 200, a modality device 300 and an HIS/RIS 400 via an electronic network. The communication controlling device 10 includes various communication protocols for different forms of networks. The electronic network referred to herein means an entire information communication network based on a telecommunication technique, and examples of the electronic network include a hospital backbone LAN, a wireless/wired LAN and the Internet as well as a telephone network, an optical fiber communication network, a cable communication network and a satellite communication network. The image interpretation report creating apparatus 100 obtains study data from the picture archiving and communication server 200 or the modality device 300 via the electronic network.

The picture archiving and communication server 200, the HIS/RIS 400 and the image interpretation report creating apparatus 100 may be configured as a cloud image interpretation report creating system. In such a case, the image interpretation report creating apparatus 100 of the image interpretation report creating system can obtain a medical image from the picture archiving and communication server 200 or the modality device 300, for example, via a network.

Examples of the modality device 300 include various kinds of modality devices such as an X-ray computed tomography (CT) device, a magnetic resonance imaging (MRI) device, a positron emission tomography (PET) device and an ultrasonic diagnostic device. Data to be input to the image interpretation report creating apparatus 100 is volume data formed by a plurality of slice images.

The image interpretation report creating apparatus 100 is connected to the HIS/RIS 400. The HIS/RIS 400 is a system that processes an inspection request or the like made by a doctor or the like, which is referred to as an inspection order. The image interpretation report creating apparatus 100 can obtain, via the electronic network, patient information including a patient ID that uniquely identifies a patient or the name, sex, build of the patient and an inspection request including details of a treatment, the type of the inspection, the purpose of the inspection or the type of the modality device. The details of the treatment include the kinds of drugs or treatments prescribed for the patient and the anamnesis of the patient.

The main control unit 30 executes a program stored in the storage unit 20 to detect the position (anatomical position) of a local structure in obtained volume data, selects a key image in creation of an image interpretation report, or extracts a local structure that is a candidate to be involved with a finding, for example. In the following description, a position in a patient coordinate system of a local structure detected in a medical image will be referred to as an anatomical position, as required.

The key image is an image that is determined by a reader as a key for image interpretation from among a plurality of images included in one piece of medical image data composed of a plurality of medical images. For one piece of medical image data, one or more images are specified as key images.

The storage unit 20 is formed by a storage medium such as a RAM or a ROM and comprises a storage medium that can be read by the main control unit 30, such as a magnetic storage medium, an optical storage medium or a semiconductor memory. Some or all of the programs and data in the storage medium may be downloaded via the electronic network. The image interpretation report creating apparatus 100 may detect the anatomical position based on a program or data stored in advance in the storage unit 20, on data or the like stored in an external storage device accessed via the communication controlling device 10 or on a program stored in an external storage device or the like.

The display unit 40 is formed by a common display device such as a liquid crystal display or an organic light emitting diode (OLED) display and displays an image under the control of the main control unit 30.

The input unit 50 is formed by a common input device such as a keyboard, a touch panel, a ten key or a mouse. The input unit 50 outputs an input signal responsive to an operation such as selection of a key image or selection of a local structure involved with a finding to the main control unit 30.

In the following, a first embodiment and a second embodiment will be described. The first embodiment relates to a case where no finding has been entered in a finding entry field when a key image is selected, and the second embodiment relates to a case where a finding, has been entered in the finding entry field when a key image is selected.

First Embodiment

The first embodiment relates an operation that occurs when a key image is selected when no finding has been entered.

(1) Configuration

Figure 2:
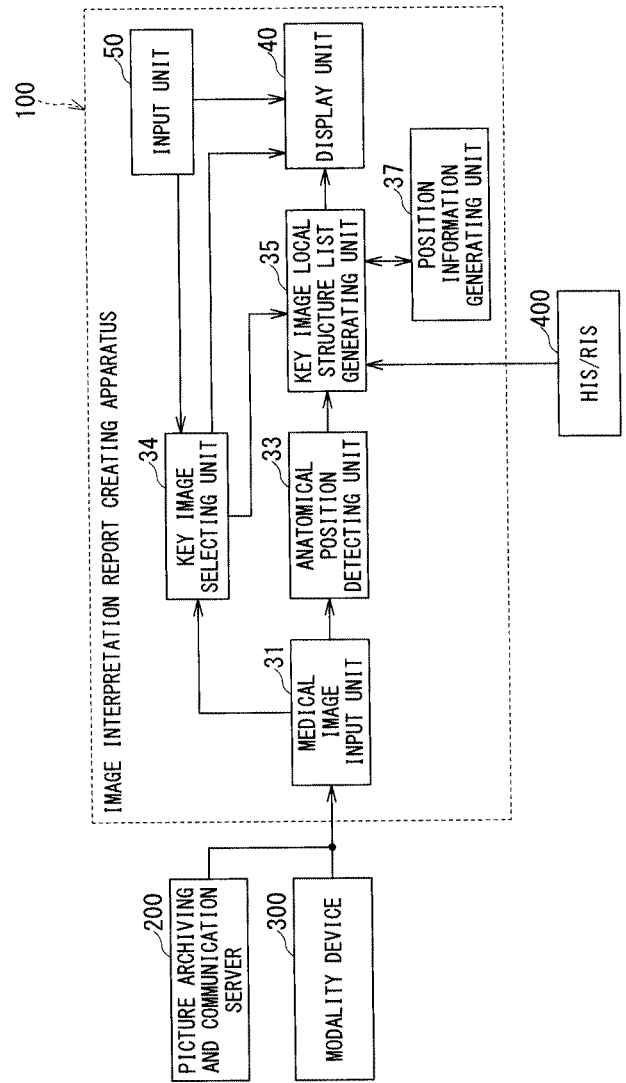
FIG. 2 is a functional block diagram showing an example of a functional configuration of the image interpretation report creating apparatus 100 according to a first embodiment.

FIG. 2 is a functional block diagram showing an example of a functional configuration of the image interpretation report creating apparatus 100 according to a first embodiment. As shown in FIG. 2, the image interpretation report creating apparatus 100 comprises a medical image input unit 31, an anatomical position detecting unit 33 serving as a position detecting unit, a key image selecting unit 34, a key image local structure list generating unit 35 serving as a first local structure information generating unit, a position information generating unit 37, the display unit 40 and the input unit 50. Of these components, the functions of the medical image input unit 31, the anatomical position detecting unit 33, the key image selecting unit 34, the key image local structure list generating unit 35 and the position information generating unit 37 are implemented by a processor of the main control unit 30 executing a program stored in the storage unit 20, for example. These functions may be implemented by a plurality of processors cooperating with each other or by a hardware logic such as a circuit without using a CPU.

The display unit 40 is composed of a function that is implemented by the main control unit 30 executing a program stored in the storage unit 20 and a display function.

Medical image data from the picture archiving and communication server 200 or the modality device 300, for example, is input to the medical image input unit 31. The medical image data may be produced by the modality device 300 in response to an inspection request from a doctor or the like, for example. The medical image data produced by the modality device 300 may be stored in the picture archiving and communication server 200 or may be input to the image interpretation report creating apparatus 100, an image display device or the like without passing through the picture archiving and communication server 200. The medical image data may be previously stored in the storage unit 20 via a portable storage medium or a network. Medical image data used for creation of an image interpretation report is input to the medical image input unit 31 of the image interpretation report creating apparatus 100.

Each of the plurality of medical images may be a bundle of a plurality of sub-images (slice images, for example) forming the medical image. For example, volume data produced based on a plurality of sub-images (slice images, for example) forming the medical image may be input to the medical image input unit 31. The volume data and the plurality of sub-images from which the volume data is produced associated with each other may be input to the medical image input unit 31 as one piece of medical image data. In the following description, the term "medical image data" and "medical image" are interchangeable with the term "volume data" in the context of inputting the volume data to the medical image input unit 31. In the context of selecting and extracting one or more of the plurality of sub-images forming a medical image, the one or more sub-images may be multi planar reconstruction (MPR) images produced based on the volume data.

The anatomical position detecting unit 33 serving as a position detecting unit detects the position (anatomical position) of a local structure for input medical image data and attaches information on the detected anatomical position (referred to as anatomical position information, hereinafter) to the medical image data. The anatomical position information may be previously attached to the input medical image data. For example, the attachment of the anatomical position information to the medical image data may occur when the modality device 300 produces an image or when the image is stored in the picture archiving and communication server 200. In that case, the detection of the anatomical position by the anatomical position detecting unit 33 can be omitted. A method in which the anatomical position detecting unit 33 detects the anatomical position will be described later.

The anatomical position information attached to the medical image data may be retained in a data format, such as XML data or binary data, and associated with corresponding medical image data or the like. The obtained medical image data complies with the digital imaging and communication in medicine (DICOM) format, and the anatomical position information may be retained as supplementary information in the DICOM standard.

The key image selecting unit 34 selects one or more sub-images as key images from among sub-images forming the input medical image in association with the image interpretation report. The key image selecting unit 34 provides information on the selected sub-images, that is, the key images, to the key image local structure list generating unit 35 serving as the first local structure information generating unit.

It is essential only that the key image is selected in association with a new image interpretation report currently being created, and the key image may not be attached to the image interpretation report. During creation of a new image interpretation report, the user can attach a key image associated with the new image interpretation report, delete a key image associated with the new image interpretation report, or otherwise make a change to the key images associated with the new image interpretation report as required.

The key image selecting unit 34 may regard a key image as being selected in association with the image interpretation report currently being created at a point in time when the user specifies the key image from among the sub-images forming the medical image, and provide the information on the key image to the key image local structure list generating unit 35 at this point in time. Alternatively, the key image selecting unit 34 may regard a key image as being selected in association with the image interpretation report currently being created at a point in time when a predetermined event occurs after the key image is specified, and provide the information on the key image to the key image local structure list generating unit 35 at this point in time. The point in time when a predetermined event occurs may be a point in time when a direct instruction from the user to establish that a key image is selected in association with the image interpretation report is received at the input unit 50, a point in time when a key image is attached to the image interpretation report, or a point in time when a predetermined time has elapsed after a key image is selected. In the following description, the operation of the key image selecting unit 34 to "select a key image in association with an image interpretation report" will be referred to simply as to an operation to "select a key image"

The key image selecting unit 34 may attach a mark to the key image at a predetermined position. For example, having selected a key image from among the plurality of sub-images forming the medical image, the user may attach, to the selected key image at a position of interest, a mark indicating that the position is a position of interest through the input unit 50. In that case, the key image selecting unit 34 can include information on the attached mark in the information on the key image when the key image selecting unit 34 provides the information on the key image to the key image local structure list generating unit 35. The information on the mark can include information on the significance of the mark and information on the position of the mark.

Upon receiving the information on the key image from the key image selecting unit 34, the key image local structure list generating unit 35 serving as the first local structure information generating part identifies at least one of a local structure in the key image or a local structure in a vicinity of the key image. If the information on the key image received from the key image selecting unit 34 includes information on a mark attached to the key image, the key image local structure list generating unit 35 may narrow down the local structures to be identified based on the distances from the mark to the local structures when identifying a local structure in a vicinity of the key image, for example. The key image local structure list generating unit 35 then generates information on the identified local structure as first local structure information and makes the display unit 40 display the information. In the following, an example in which the first local structure information is local structure information in a list format (referred to as a key image local structure list, hereinafter) will be described.

For example, the key image local structure list generating unit 35 identifies the position of at least one of the local structure in the key image selected by the key image selecting unit 34 and the local structure in a slice image in a vicinity of the key image, and generates a list (key image local structure list) of the local structures that correspond to the identified anatomical position. In addition, the key image local structure list generating unit 35 narrows down or rearranges the local structures in the key image local structure list based on the inspection request or information created by the position information generating unit 37. A processing performed by the key image local structure list generating unit 35 will be described later.

The position information generating unit 37 calculates the distances from local structures in the list in the first local structure information (key image local structure list) to the key image. If a coordinate of the key image with respect to an anatomical position or a coordinate of an annotation in the key image is given, for example, the distance to the coordinate is calculated as the distance to the key image. If the information on the key image received from the key image selecting unit 34 includes information on a mark attached to the key image, the key image local structure list generating unit 35 can also determine the distances from the positions of the local structures in the key image local structure list to the mark in the key image.

The annotation is a symbol, such as an arrow, or a line enclosing a region that is displayed on the key image to indicate a part of the key image that should be observed with care. A method in which the position information generating unit 37 calculates a distance will be described later.

The display unit 40 displays the key image local structure list in addition to the key image. Furthermore, the display unit 40 displays a finding in response to selection in the key image local structure list through the input unit 50. Display of a finding will be described later.

(2) Operation

Figure 3:
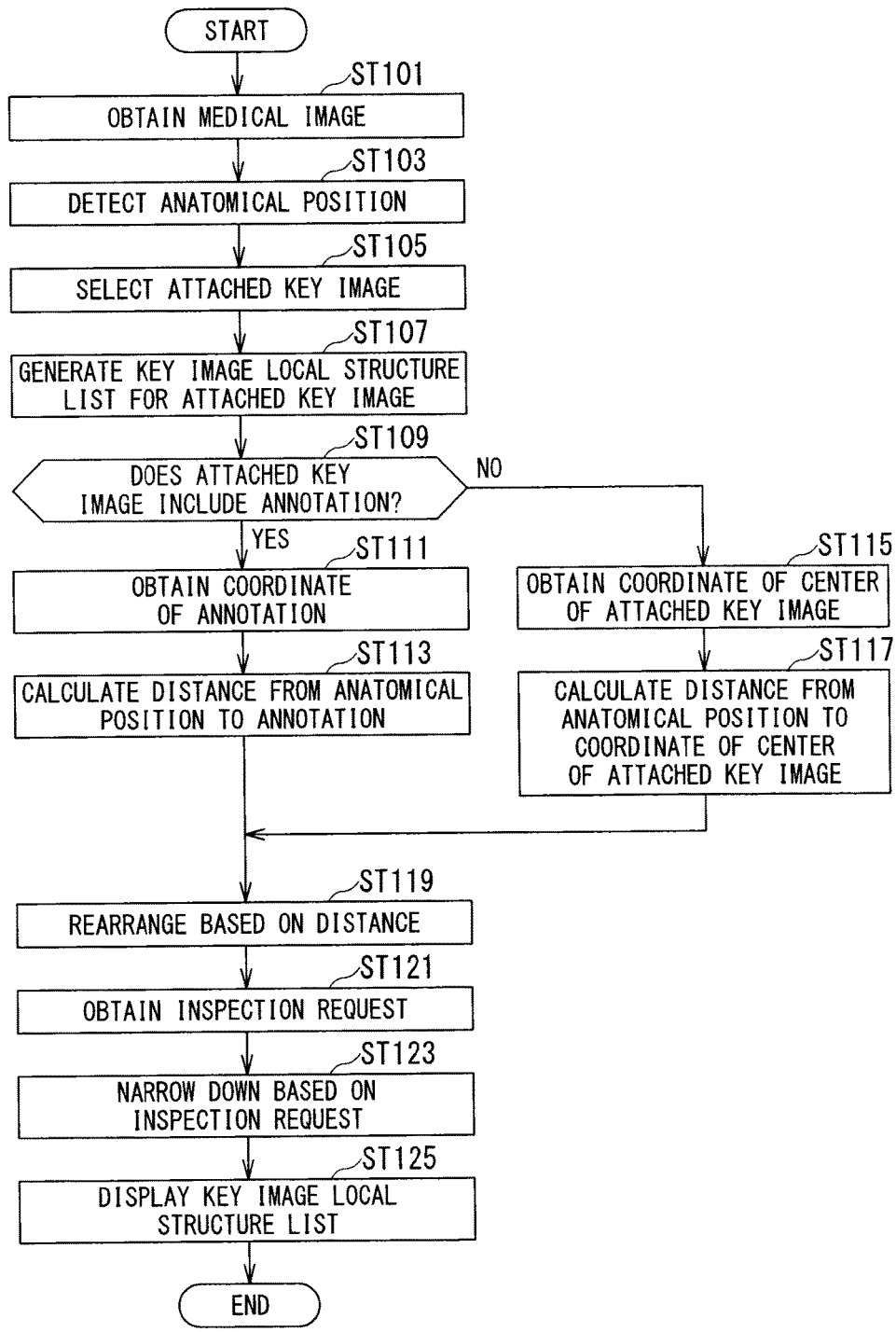
FIG. 3 is a flowchart showing an example of an operation of the image interpretation report creating apparatus 100 according to a first embodiment.

FIG. 3 is a flowchart showing an example of an operation of the image interpretation report creating apparatus 100 according to a first embodiment. FIG. 3 shows an example of a procedure of generating an anatomical chart with an imaging range image.

In ST101, medical image data composed of a plurality of images is input to the medical image input unit 31 from the picture archiving and communication server 200 or the modality device 300. For example, the medical image data is volume data produced based on a plurality of sub-images (slice images, for example) forming a medical image corresponding to the medical image data. Alternatively, the volume data and the plurality of sub-images from which the volume data is produced associated with each other may be input to the medical image input unit 31 as one piece of medical image data.

In ST103, the anatomical position detecting unit 33 detects an anatomical position for the input medical image data.

Figure 4A:
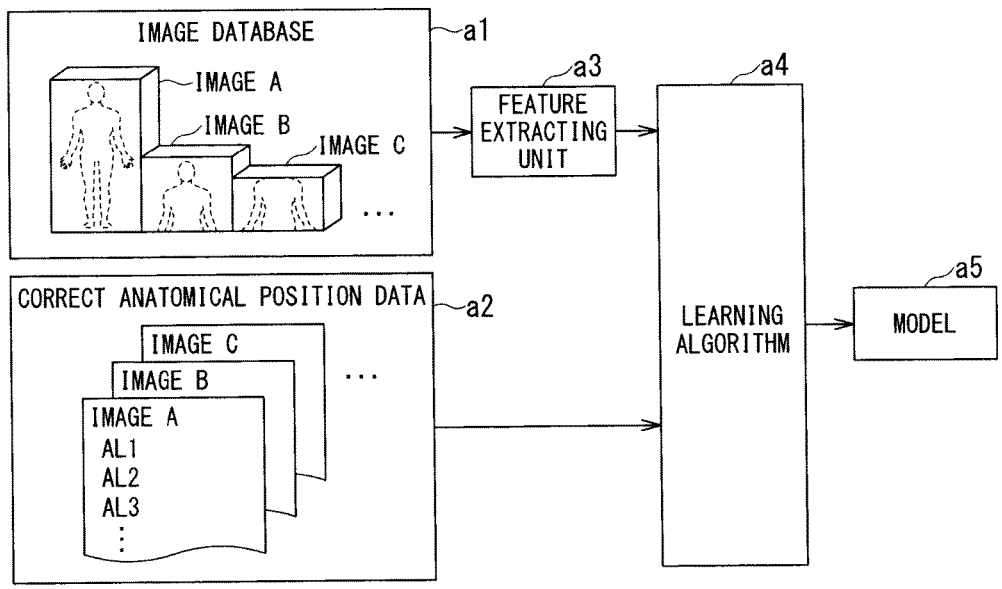
FIG. 4A shows an example of a method of producing a model a5 used for detecting an anatomical position.

FIG. 4 are diagrams for illustrating a method of detecting an anatomical position. FIG. 4A shows an example of a method of producing a model a5 used for detecting an anatomical position. The model a5 shown in FIG. 4A may be previously stored in the storage unit 20 of the image interpretation report creating apparatus 100 or in an external storage device.

As shown in FIG. 4A, the model 5a used for detecting an anatomical position is produced by common machine learning or pattern recognition. FIG. 4A shows an example in which the model a5 is produced using an image database a1 and correct anatomical position data a2. The image database a1 is a collection of volume data obtained by an X-ray CT apparatus or an MRI apparatus for various objects of different body shapes. As illustrated in FIG. 4A, the image database a1 includes not only the volume data on a whole body (image A) but also volume data of an image of a part of a body (images B and C). The correct anatomical position data a2 is data on a correct anatomical position previously determined by an expert such as a doctor for each image in the image database a1. As shown in FIG. 4A, a feature extracting unit a3 extracts a feature from each piece of volume data in the image database a1, and a learning algorithm a4 produces the model a5 using the correct anatomical position data a2. The model a5 is used to associate the feature extracted from the image database a1 with an anatomical position. The model a5 is a model based on machine learning, for example. Different models a5 may be produced for different sexes, ages, races or builds, or a single model a5 that accommodates for such differences may be produced.

Figure 4B:
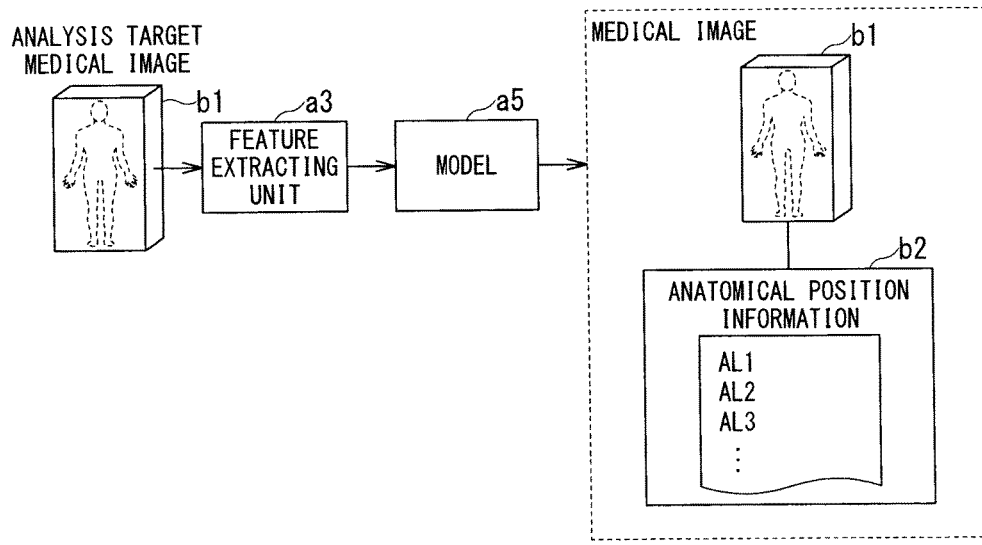
FIG. 4B shows an example of a process performed by the anatomical position detecting unit.

FIG. 4B shows an example of a process performed by the anatomical position detecting unit 33. As with the feature extracting unit a3 shown in FIG. 4A, the anatomical position detecting unit 33 extracts a feature from analysis target image data b1 for which the anatomical position is unknown, and detects the anatomical position using the model a5 already produced. More specifically, the anatomical position detecting unit 33 detects a local structure in the medical image and calculates the position of the detected local structure in the medical image as the anatomical position. Anatomical position information b2 thus calculated is added to the analysis target image data b1.

The anatomical position described above is not exclusively detected in the process described above and can also be detected with a mathematical statistic framework referred to as computational anatomy (computational anatomical model).

FIG. 5 are diagrams for illustrating kinds of local structures. A local structure is a characteristic structure in the human body that is important for understanding a medical image and is sometimes referred to as an anatomical landmark (AL). For example, FIG. 5A shows examples of local structures of a head and a neck. From the top to the bottom of the list, FIG. 5A shows an anterior arch (tubercle) of atlas (cervical vertebra I), a superior tip of dens/peg (cervical vertebra II), a superior aspect of right eye globe, a superior aspect of left eye globe, a center of a right eye globe and a center of a left eye globe. Similarly, FIG. 5B shows, as local structures of a chest, a bifurcation of trachea, an apex of a right lung, an apex of a left lung, an inferior angle of a right scapula, an inferior angle of a left scapula and a start of left subclavian artery (branching off aortic arch). FIG. 5C shows, as local structures of an abdomen, a superior pole of a right kidney, a superior pole of a left kidney, an inferior pole of a right kidney, an inferior pole of a left kidney, a head of a pancreas and a tip of a tail of a pancreas. FIG. 5D shows, as local structures of lower limbs, a lateral epicondyle of a right femur, a medial epicondyle of a right femur, a lateral epicondyle of a left femur, a medial epicondyle of a left femur, a lateral condyle of a right tibia and a medial condyle of a right tibia. Local structures of a whole body are defined with the grading shown in FIG. 5, for example and a plurality of local structures are defined for each of various bones, muscles, viscus or the like of the human body. The anatomical position is detected for each of these local structures.

The anatomical position is retained in a state where the anatomical position is associated with the medical image data as the anatomical position information. For example, the anatomical position information may be retained as a database in the storage unit 20 or the like in an XML or text format, for example, in a state where the anatomical position information is associated with an ID or the like that uniquely identifies the medical image. Alternatively, the anatomical position information may be retained in a state where the anatomical position information is integrated with the medical image data as supplementary information in DICOM.

The anatomical position information can include not only the information on the anatomical position but also site information on the chest, the abdomen or the like to which the local structure corresponding to the anatomical position belongs and body tissue information on a functional system in the human body, such as a skeletal system or a respiratory system, to which the local structure corresponding to the anatomical position belongs, for example.

Figures 6A, 6B:
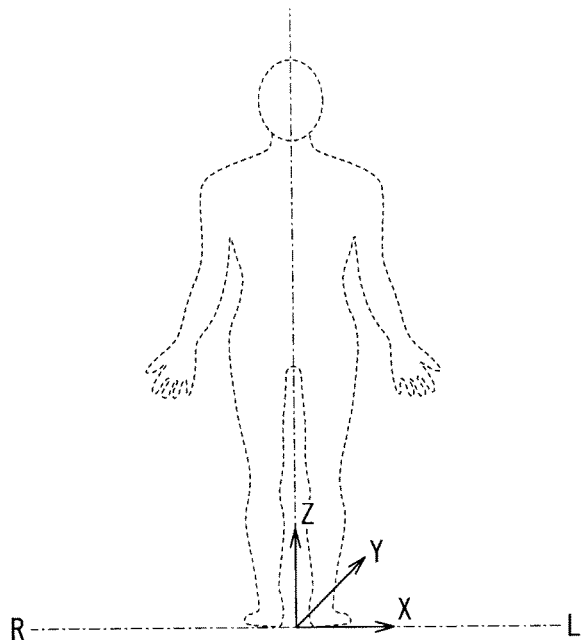
FIG. 6A shows an example of the anatomical position information.
FIG. 6B is a diagram for illustrating a patient coordinate system.

FIG. 6 are diagrams for illustrating the anatomical position information. The table of FIG. 6A shows an example of the anatomical position information. From the left to the right, as the anatomical position information, the table of FIG. 6A shows an identifier, a name, a reliability, a site, a body tissue, positions in a patient coordinate system (X-axis, Y-axis and Z-axis) of an anatomical position. FIG. 6A shows part of the anatomical position information on the abdomen, as an example. From the left to the right, the first row of the table of FIG. 6A shows an identifier (ABDO25. C), a name (center of body of L5), a reliability (0.87), a site (abdomen), a body tissue (skeletal system), positions in a patient coordinate system (X-axis (−3.1), Y-axis (23.4), Z-axis (90.0)). Similarly, a second row of the table shows an identifier (ABDO32. C), a name (superior aspect of right iliac spine), a reliability (0.82), a site (abdomen), a body tissue (skeletal system), positions in a patient coordinate system (X-axis (−11.1), Y-axis (−54.4), Z-axis (84.1)), and a third row of the table shows an identifier (ABDO39. C), a name (superior aspect of left iliac spine), a reliability (0.83), a site (abdomen), a body tissue (skeletal system), positions in a patient coordinate system (X-axis (−3.0), Y-axis (30.0), Z-axis (104.0)).

The identifier is an ID that uniquely identifies the anatomical position. The name is a name of the local structure and is represented by a technical term of anatomy or medicine. The reliability is a numerical value that indicates the precision of the anatomical position. Since the anatomical position is data computationally estimated by a machine learning algorithm or pattern recognition, the numerical value that indicates the precision of the computation of the position is used. In the example shown in FIG. 6A, the numerical value ranges from 0 to 1, and the closer to 1, the higher the reliability is. The site refers to a site of the human body to which the local structure belongs and means a sort such as chest or abdomen. The body tissue is sorted based on the function of the local structure and is represented by the nerve system, the skeletal system or the respiratory system, for example. Furthermore, a viscus name, such as heart, lung or femur, or information on an anatomical structural unit other than the site or the body tissue may be provided as the anatomical position information. The positions in the patient coordinate system are X-axis, Y-axis and Z-axis coordinates that indicate the anatomical position.

FIG. 6B is a diagram for illustrating a patient coordinate system. As shown in FIG. 6B, the patient coordinate system is a coordinate system whose X-axis extends in a left-right direction of the patient, whose Y-axis extends in a dorsal-ventral direction of the patient, and whose Z-axis extends in a head-foot direction of the patient. The X coordinate increases as it goes from the center of the body of the patient to the right, the Y coordinate increases as it goes from the center of the body of the patient to the dorsal side, and the Z coordinate increases as it goes from the foot to the head of the patient. The positions in the patient coordinate system are relatively expressed with respect to an arbitrary position, such as a reference position included in the volume data.

Note that FIG. 6 show just an example of the anatomical position information and the data format thereof.

Description with reference to FIG. 3 will be resumed.

In ST105, a key image is selected from among a plurality of sub-images displayed on the display unit 40 is selected through the input unit 50.

It is essential only that the key image is selected from among a plurality of sub-images forming the medical image and associated with the new image interpretation report currently being created by the key image selecting unit 34, and the key image may not be attached to the image interpretation report. In the following, an example will be described in which the key image selecting unit 34 provides information on the key image to the key image local structure list generating unit 35 when the key image is attached to the image interpretation report, that is, in a case where the key image is an attached key image. The key image attached to the image interpretation report will be referred to as an attached key image, hereinafter. In the case where the key image is attached to the image interpretation report, the key image selecting unit 34 provides information on the attached key image as the information on the key image to the key image local structure list generating unit 35.

In ST107, the key image local structure list generating unit 35 searches for the anatomical position for the attached key image and generates a key image local structure list (first local structure information) for the attached key image.

The medical image data is volume data containing a plurality of slice images, for example. The key image is a slice image selected from the medical image data input to the medical image input medical image input unit 31, and one or more slice images may be selected from the medical image data as the key image(s). The medical image data contains anatomical positions identified by the anatomical position detecting unit 33 and contains anatomical position information shown as an example in FIG. 6A. The key image local structure list for the key image is created from the anatomical position information described above.

Figure 7:
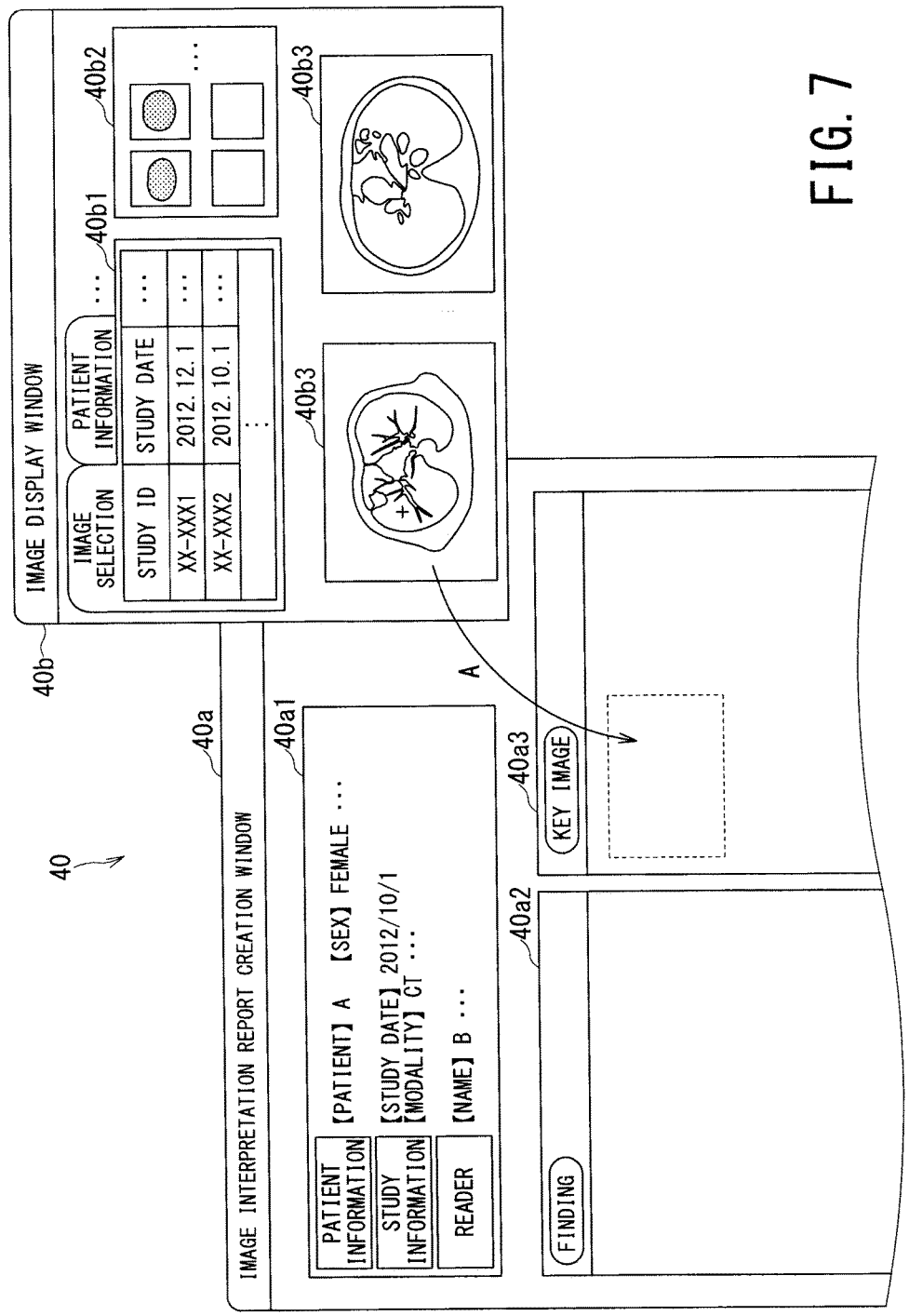
FIG. 7 is a diagram for illustrating selection of a key image in the image interpretation report creating apparatus 100 according to the first embodiment.

FIG. 7 is a diagram for illustrating selection of a key image in the image interpretation report creating apparatus 100 according to the first embodiment. FIG. 7 shows an example in which the display unit 40 displays an image interpretation report creation window 40a and an image display window 40b.

In the image display window 40b, a key image 40b3 and a medical thumbnail field 40b2 that displays a plurality of images contained in the medical image data input to the medical image input unit 31 are displayed. The displayed key image 40b3 is an image selected from the medical image data by the key image selecting unit 34. A study information field 40b1 displays a list of images that can be displayed in the image display window 40b or patient information, for example.

In the image interpretation report creation window 40a, a study information field 40a1 displays patient information, study information included in an inspection request, the name of a reader or the like. In the image interpretation report creation window 40a, a finding entry field 40a2 that is a region in which a finding is entered and a key image attachment region 40a3 that is a region for attachment of a key image are also shown as examples. The finding entry field 40a2 is a text area, for example, and displays a character string or the like entered through the input unit 50 composed of a keyboard, a mouse or the like. A key image selected on the image display window 40b is moved into the region shown by the dashed line in the key image attachment region 40a3 for attachment to the image interpretation report. For example, the key image displayed in the image display window 40b can be attached to the image interpretation report by moving the key image into the key image attachment region 40a3 by a drag-and-drop operation with an input device such as a mouse. Alternatively, the key image displayed in the image display window 40b can also be attached to the image interpretation report by pressing the image display window 40b at the position of the key image. The key image selected from among a plurality of key images and moved into the key image attachment region 40*a*3 by such an operation will be referred to as an attached key image.

Once the attached key image is moved into the key image attachment region 40*a*3 by the operation described above with reference to FIG. 7, the key image local structure list generating unit 35 extracts an anatomical position for the attached key image. The key image local structure list generating unit 35 extracts an anatomical position included in the attached key image or an anatomical position included in a slice image in a vicinity of the attached key image. Information on the key image 40*b*3 yet to be moved into the key image attachment region 40*a*3 may be provided to the key image local structure list generating unit 35. In that case, the key image local structure list generating unit 35 extracts an anatomical position for the key image 40*b*3.

Figures 8A, 8B:
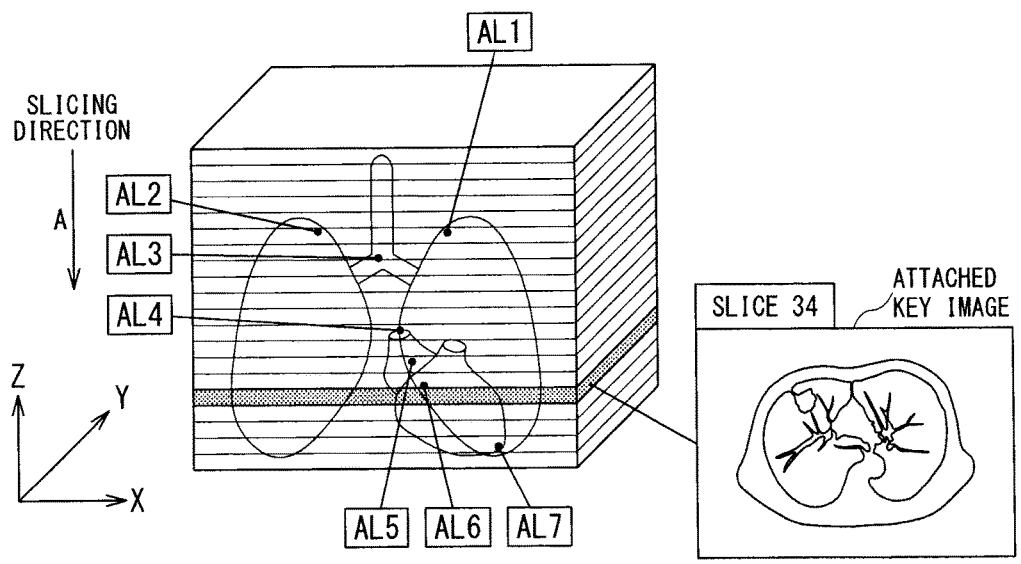
FIG. 8A is a diagram for illustrating generation of a key image local structure list for an attached key image in the image interpretation report creating apparatus 100 according to the first embodiment.
FIG. 8B shows an example of the key image local structure list for the attached key image.

FIG. 8 are diagrams for illustrating generation of a key image local structure list for an attached key image in the image interpretation report creating apparatus 100 according to the first embodiment. The left diagram of FIG. 8A shows an example of the medical image data, and the right diagram of FIG. 8A shows an attached key image. In the example shown in the right diagram of FIG. 8A, the slice number of the attached key image is "34".

The attached key image lies at the position shown by hatching in the medical image data shown in the left diagram of FIG. 8A. In the medical image data, a plurality of anatomical positions are detected. In the example shown in the left diagram of FIG. 8A, seven anatomical positions shown by black dots are detected in the medical image data. In the example shown in FIG. 8A, local structures that correspond to the anatomical positions are denoted by AL1, AL2, AL3, AL4, AL5, AL6 and AL7.

As shown in the left diagram of FIG. 8A, supposing that a Z-axis extends in a slicing direction of the medical image data, a slice image corresponds to an X-Y plane. The medical image data includes information on an imaging condition as supplementary information. The imaging condition include a pixel size, a slice thickness, a slice interval, an imaging start position or a reference position, for example. As described above with reference to FIG. 6A, the anatomical position is indicated in a coordinate system referred to as a patient coordinate system. Supposing that the Z-axis extends in the slicing direction of the medical image data, a coordinate of the anatomical position in the patient coordinate system can be transformed into a voxel coordinate of the medical image data, or a coordinate of a slice image and a slice number, based on the information such as the pixel size, the slice thickness or the slice interval.

FIG. 8B shows an example of the key image local structure list for the attached key image. From the left to the right, the table of FIG. 8B shows a local structure, coordinates and a slice number for each of the anatomical positions shown in FIG. 8A. FIG. 8B shows an example in which anatomical positions are represented by coordinates and slice numbers of the slice images. In the example shown in FIG. 8A, of the seven anatomical positions identified for the medical image data, five anatomical positions in a vicinity of the attached key image are extracted. In this way, in the key image local structure list, anatomical positions that exist in at least one of the attached key image and the slice image(s) in the vicinity of the key image are extracted. For example, anatomical positions included in a dozen or so slice images preceding and following the slice image of the attached key image may be extracted, or anatomical positions may be extracted based on the site or structure to which the anatomical position for the attached key image belongs. As described above with reference to FIG. 6A, the anatomical position information includes site information on a site to which an anatomical position belongs, such as the chest or the abdomen, and information on classification of structures of the human body, such as the heart or the liver. Based on these pieces of information, to what site or viscus the attached key image belongs can be determined. A list of local structures that correspond to the site or viscus to which the anatomical positions belong may be produced as the key image local structure list.

If the key image local structure list for the key image (attached key image, for example) extracted as described above is displayed in the finding entry field 40*a*2 shown in FIG. 7, the local structure can be simply selected from the list, and entry of the anatomical position relating to the finding can be omitted.

In addition to the function, the image interpretation report creating apparatus 100 according to this embodiment can calculate distances from the key image (attached key image, for example) to the anatomical positions that correspond to the local structures shown in the key image local structure list, and add the calculated distances to the key image local structure list. In addition, the key image local structure list generating unit 35 may narrow down, or adjust the order of display of, the local structures shown in the key image local structure list based on at least any of information on a site to be inspected, information on a purpose of an inspection and information on details of a treatment included in the inspection request.

The description with reference to the flowchart of FIG. 3 will be resumed.

In ST109, the position information generating unit 37 determines whether the key image includes an annotation or not. If the key image includes an annotation, the process proceeds to ST111, in which a coordinate of the annotation in the attached key image is obtained. If the key image includes no annotation, the process proceeds to ST115, in which a center coordinate of the attached key image is obtained. Although the center coordinate is used as the coordinate of the attached key image for distance calculation in this embodiment, the coordinate used for distance calculation is not limited to the center coordinate. The position information generating unit 37 may calculate the length of a perpendicular from the anatomical position to the key image as the distance, for example.

In ST113, the position information generating unit 37 calculates the distance from each of the anatomical positions that correspond to the local structures in the key image local structure list for the attached key image to the coordinate of the annotation in the attached key image obtained in ST111.

In ST117, the position information generating unit 37 calculates the distance from each of the anatomical positions that correspond to the local structures in the key image local structure list for the attached key image to the center coordinate of the attached key image obtained in ST115.

In ST119, the key image local structure list generating unit 35 generates a key image local structure list by changing the order of display of the local structures based on the information on the distances generated by the position information generating unit 37. Alternatively, the key image local structure list generating unit 35 may narrow down the local structures based on the calculated distances. For example, the heart is said to have a dimension of approximately 12 cm to 15 cm. Thus, such a typical size of each viscus is used as a threshold, and a local structure at a distance greater than the threshold may be delisted.

Alternatively, a representative position for each structure, such as a viscus or a bone, may be determined, and the local structures in the key image local structure list may be narrowed down based on the relative position with respect to the representative position. The representative position may be the center coordinate of the viscus or the like or other appropriate position that depends on the indefinite shape of the viscus. Alternatively, the representative position may be determined based on the nature or function of the viscus. For example, in some cases, a mixture of anatomical positions that belong to various viscera such as the liver, the heart and the lungs is identified as anatomical positions in the attached key image and slice images in the vicinity of the key image. In such cases, even an anatomical position identified as being in the vicinity of the attached key image can belong to a viscus that is only slightly related to the attached key image. To cope with such a situation, for example, a representative position of each of the viscera to which the anatomical positions in the attached key image belong can be determined from anatomical positions that represent the upper end and the lower end of the viscus, a viscus whose representative position is far from the anatomical position closest to the attached key image can be identified, and the local structure that corresponds to the anatomical positions that belong to the viscus can be excluded from the key image local structure list. In this way, the local structures in the key image local structure list can be narrowed down depending on the representative position of the viscus or the like, and a local structure that corresponds to an anatomical position that belongs to a viscus that is only slightly related to the attached key image may be excluded from the key image local structure list.

In ST121, the key image local structure list generating unit 35 receives an inspection request from the HIS/RIS 400. The inspection request includes information on a site to be inspected, a purpose of the study, a drug prescribed, details of a treatment, or anamnesis, for example.

In ST123, the key image local structure list generating unit 35 uses the study information to narrow down the local structures in the key image local structure list. For example, a local structure that is related to a site or viscus that is outside of the site to be inspected or the purpose of the study can be excluded from the key image local structure list. On the other hand, a local structure that corresponds to a site or viscus for which the anamnesis indicates the possibility of metastasis or a complication can be added to the key image local structure list.

In ST125, the key image local structure list for the attached key image generated by the key image local structure list generating unit 35 is displayed on the display unit 40.

The steps ST119 to ST123 can be performed in any order. Furthermore, any of the steps may be solely performed, or a plurality of the steps may be performed in combination.

Figure 9A:
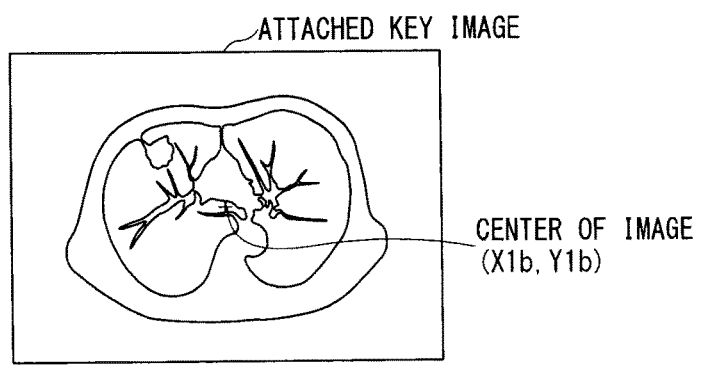
FIG. 9A is a diagram for illustrating coordinates of the center of the attached key image used as reference points in calculation of the distance between the attached key image and the anatomical position.

FIG. 9 are diagrams for illustrating coordinates used as reference points in calculation of the distance between the attached key image and the anatomical position in the image interpretation report creating apparatus 100 according to the first embodiment. The position information generating unit 37 obtains coordinates of the center of the attached key image or coordinates of the annotation imparted to the attached key image. The cross symbol in FIG. 9A shows the coordinates of the center of the attached key image. In the example shown in FIG. 9A, the coordinates of the attached key image are expressed as (X1b, Y1b) in the X-Y plane, which is the plane of the slice image.

Figure 9B:
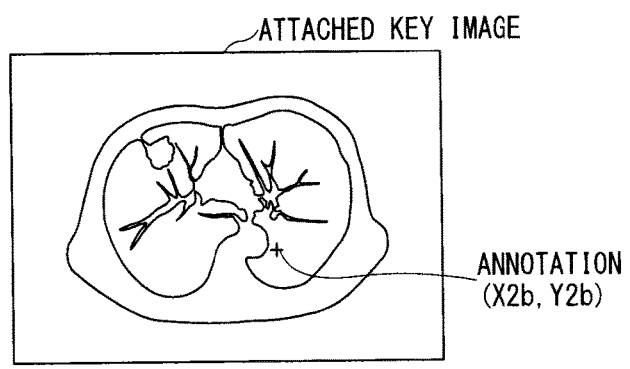
FIG. 9B is a diagram for illustrating coordinates of the annotation imparted to the attached key image used as reference points in calculation of the distance between the attached key image and the anatomical position.

The cross symbol in FIG. 9B shows the coordinates of the annotation imparted to the attached key image. In the example shown in FIG. 9B, as in the example shown in FIG. 9A, the coordinates of the annotation are expressed as (X2b, Y2b) in the X-Y plane, which is the plane of the slice image. The annotation in the attached key image may be represented as a region of a certain size.

Figure 9C:
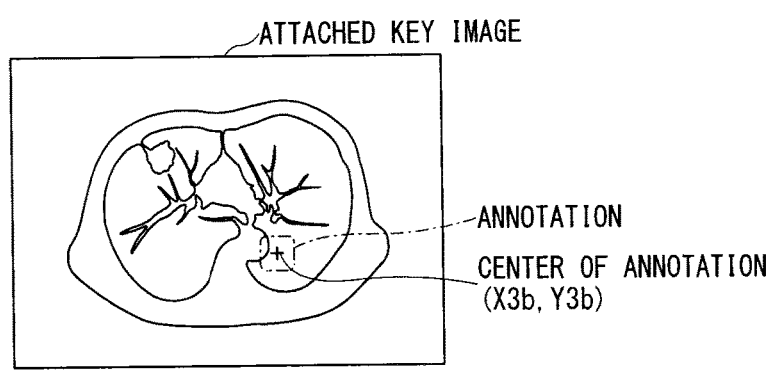
FIG. 9C is a diagram for illustrating coordinates of the center of the region specified as the annotation used as reference points in calculation of the distance between the attached key image and the anatomical position.

FIG. 9C shows an example in which the annotation is represented as a rectangular frame. The region of the annotation may be a rectangular frame such as one shown in FIG. 9C, a circular frame or a frame of any other shape arbitrarily input by the user. When the annotation is specified as a region of a certain size, the coordinates of the center of the region specified as the annotation may be used as representative coordinates of the annotation, as shown in FIG. 9C. As in the example shown in FIG. 9A, the coordinates of the annotation in the attached key image in FIG. 9C are expressed as (X3b, Y3b).

The distance from each of the anatomical positions that correspond to the already generated local structures in the key image local structure list for the attached key image to the coordinates of the center of the attached key image or the coordinates of the annotation described above with reference to FIG. 9 is calculated. The present invention is not limited to the examples described above with reference to FIG. 9, and the distance from an anatomical position to predetermined coordinates in the attached key image, such as the coordinates of a pointer or cursor input through the input unit 50 or the coordinates of a viscus to be inspected in the attached key image, can also be calculated.

Figure 10:
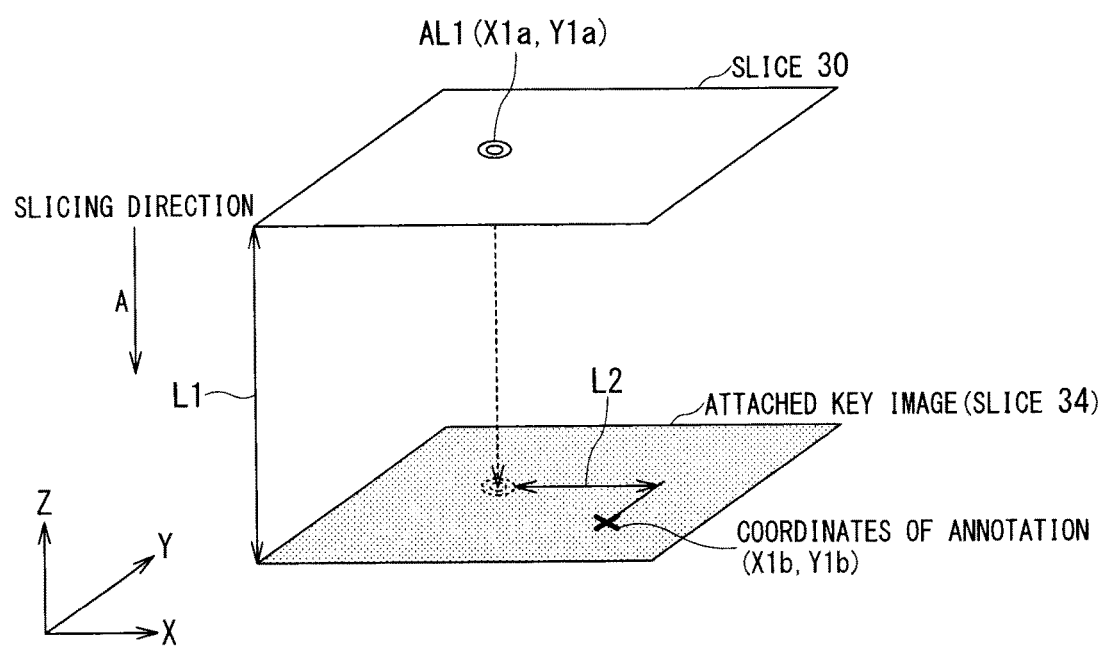
FIG. 10 is a diagram for illustrating a distance calculating method performed by the image interpretation report creating apparatus 100 according to the first embodiment.

FIG. 10 is a diagram for illustrating a distance calculating method performed by the image interpretation report creating apparatus 100 according to the first embodiment. With reference to FIG. 10, a method of calculating the distance from an anatomical position AL1 in the key image local structure list for the attached key image shown in FIG. 8B will be described as an example.

FIG. 10 shows a slice 30 that shows a cross section including the anatomical position AL1 and a slice 34 that shows a cross section that is the attached key image. AS shown in FIG. 10, the coordinates of the anatomical position AL1 are (X1a, Y1a), and the coordinates of the annotation in the attached key image are (X1b, Y1b). Supposing that the imaging conditions included in the supplementary information or the like in the medical image data are that the patient is imaged in the face-up position, and the slicing direction for the medical image data is the direction from the head to the foot of the patient, the Z-axis is the head-foot direction, the X-axis coordinate increases as it goes in the right hand direction of the patient, and the Y-axis coordinate increases as it goes in the dorsal direction of the patient.

Reference symbol L1 shown in FIG. 10 denotes the distance between the coordinates of the anatomical position AL1 and the coordinates of the annotation in the Z-direction. The distance between the Z-axis coordinate of the anatomical position AL1 and the Z-axis coordinate of the annotation can be calculated from the difference in slice number between the anatomical position AL1 and the annotation, the slice thickness and the slice interval. For example, suppose that the slice thickness is 1 cm, and the slice interval, which indicates the distance between the start positions of consecutive slice images, is 1 cm. Then, since the difference in slice number is 4 in the example shown in FIG. 10, the distance is calculated to be 4 cm. Since the direction in which the Z-axis coordinate increases can be obtained from the imaging conditions, it can be seen that the annotation of the key image is "at a distance of 4 cm in the foot direction from the anatomical position AL1" in the example shown in FIG. 10.

Reference symbol L2 shown in FIG. 10 denotes the distance between the coordinates of the anatomical position AL1 and the coordinates of the annotation in the X-axis direction. The distance can also be calculated from the difference in X-axis coordinate between the anatomical position AL1 and the annotation and the pixel size. The distance in the Y-axis direction can also be calculated in the same way.

The plurality of distances shown in FIG. 10 can be combined to describe the annotation of the attached key image as "being at a distance of 4 cm in the foot direction of the patient, 2 cm in the right hand direction, and 1 cm in the ventral direction from the anatomical position AL1".

The key image local structure list generating unit 35 generates the key image local structure list for the attached key image in the manner described above, and displays the list on the display unit 40.

Figure 11:
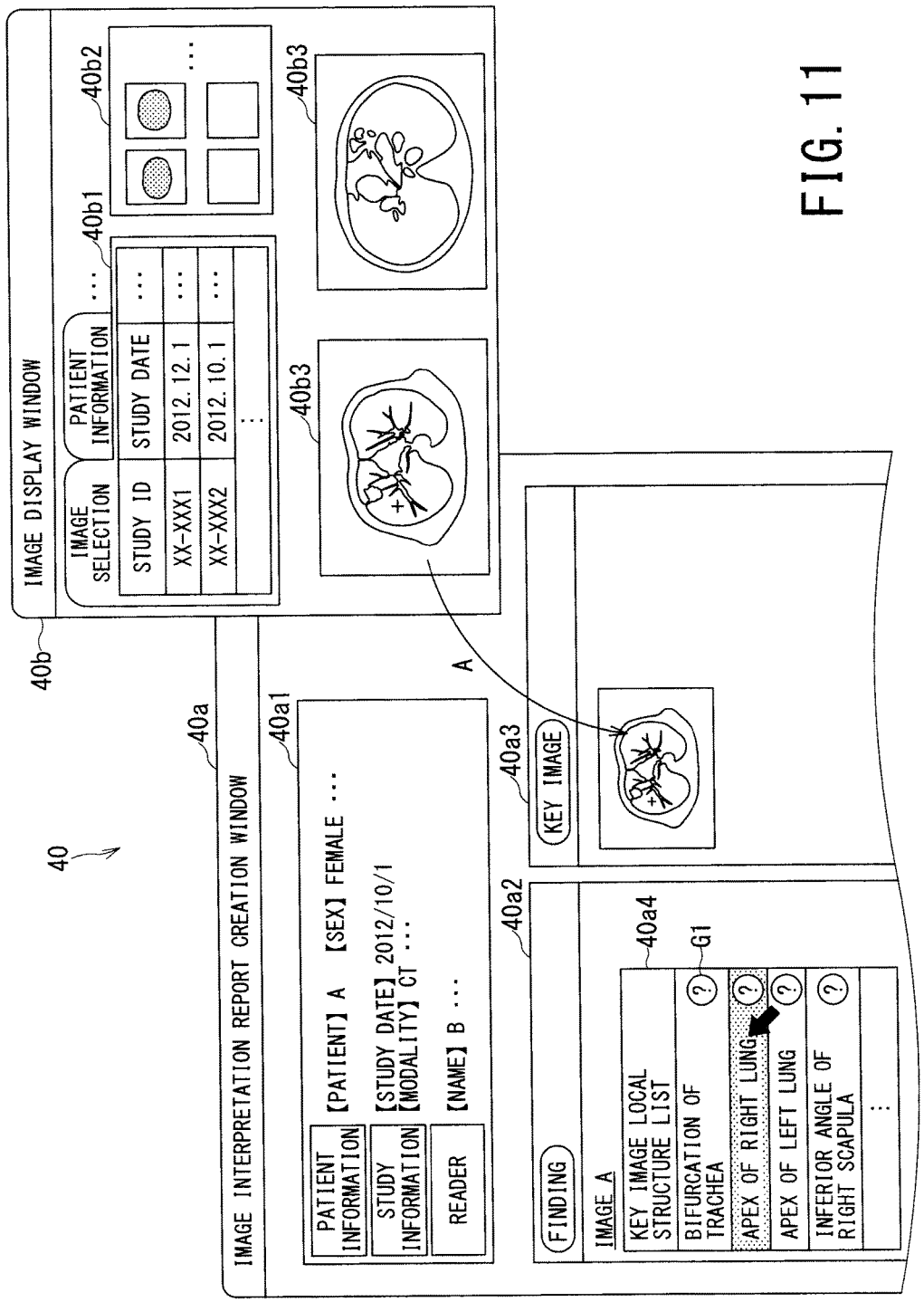
FIG. 11 is a diagram for illustrating an example of how the key image local structure list is displayed in the image interpretation report creating apparatus according to the first embodiment.

FIG. 11 is a diagram for illustrating an example of how the key image local structure list is displayed in the image interpretation report creating apparatus according to the first embodiment. A key image local structure list 40a4 shown in FIG. 11 contains anatomical positions extracted for the key image. In the example shown in FIG. 11, the key image 40b3 in the image display window 40b has been moved into the key image attachment region 40a3 of the image interpretation report creation window 40a. The key image local structure list 40a4 shown in FIG. 11 is an example of the key image local structure list for the attached key image. As shown in FIG. 11, once the attached key image is moved into the image interpretation report creation window 40a, a description of the attached key image and the key image local structure list are displayed in the finding entry field 40a2. In the example shown in FIG. 11, the attached key image is denoted as an "image A", and a text "IMAGE A" is automatically displayed. Below the text that describes the attached key image, the key image local structure list 40a4 is displayed. The user can select a local structure included in the attached key image (or the local structure closest to the attached key image) from the displayed key image local structure list 40a4, and then the local structure required to describe the finding observed in the attached key image can be automatically input. For example, in the example shown in FIG. 11, the "APEX OF RIGHT LUNG" in the key image local structure list 40a4 is hatched. In this way, the reader or the like can input the local structure to be entered in the finding entry field 40a2 to describe the attached key image simply by selecting the local structure.

Furthermore, for each of the local structures displayed in the key image local structure list 40a4, a reference literature or an anatomical dictionary can be referred to. For example, in response to a button G1 being pressed down, a reference literature concerning the local structure can be displayed to show cases relating to the local structure, or a relevant anatomical site retrieved from the anatomical dictionary can be displayed. Such reference literatures or the like may be stored in the storage unit 20 of the image interpretation report creating apparatus 100, downloaded from an external storage device, or referred to in the external storage device. Furthermore, result of searching of the Internet concerning the local structure may be displayed. As described above, when entering a finding, the user, such as a reader, can obtain various kinds of information from the image interpretation report creating apparatus 100 by investigating the local structure relating to the attached key image.

Figure 12:
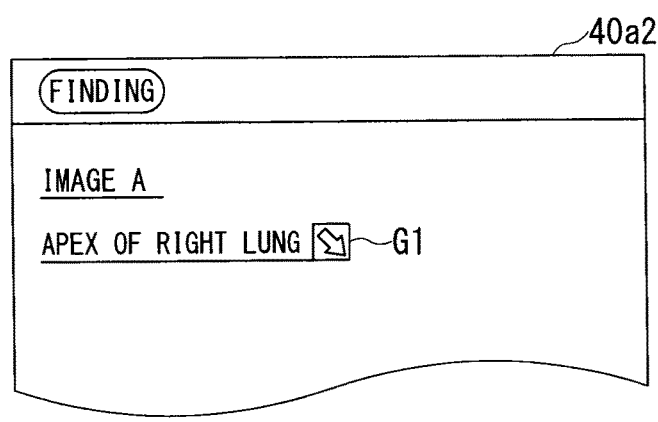
FIG. 12 is a diagram for illustrating an example in which a local structure selected from the key image local structure list is displayed in the finding in the image interpretation report creating apparatus 100 according to the first embodiment.

FIG. 12 is a diagram for illustrating an example in which a local structure selected from the key image local structure list is displayed in the finding in the image interpretation report creating apparatus 100 according to the first embodiment. FIG. 12 shows an example of the display after "APEX OF RIGHT LUNG" is selected from the key image local structure list 40a4 shown in FIG. 11. In the finding entry field 40a2, the text "APEX OF RIGHT LUNG", which is the local structure selected in the example shown in FIG. 11, is automatically displayed. The button G1 is displayed at a side of the text "APEX OF RIGHT LUNG" in FIG. 12. The key image local structure list 40a4 shown in FIG. 11 may be displayed again in response to the button G1 being pressed down.

FIG. 13 are diagrams for illustrating other examples of how the key image local structure list is displayed in the image interpretation report creating apparatus 100 according to the first embodiment. Although FIG. 11 shows an example in which only the list of local structures is displayed, distances calculated by the position information generating unit 37 may displayed in addition to the list of local structures as shown in FIG. 13A. For example, as position information on the "APEX OF RIGHT LUNG" in the second row hatched in the FIG. 13A, "AAA cm in A direction" is displayed. This means that the coordinates of the center of the attached key image or the coordinates of the annotation are at a distance of "AAA cm in A direction" from the local structure "APEX OF RIGHT LUNG". On the other hand, the position information on the "BIFURCATION OF TRACHEA" displayed in the first row is shown as "–". This means that the coordinates of the center of the attached key image or the coordinates of the annotation lie at the bifurcation of trachea. The local structures in the key image local structure list may be rearranged based on the position information. For example, the local structures may be displayed in ascending order of distance.

FIG. 13B shows an example in which checkboxes are used for selection of a plurality of local structures. In the example shown in FIG. 13B, the "APEX OF RIGHT LUNG" and the "INFERIOR ANGLE OF RIGHT SCAPULA" are selected. The anatomical position in the finding can be more stereoscopically described by using a plurality of local structures.

FIG. 13C shows an example in which sort buttons G1 to select whether to display in ascending order or descending order are provided in item name fields of the list. For example, if the sort button G1 provided in the landmark list, the local structures can be rearranged in ascending or descending alphabetical order of the names of the local structures. Alternatively, the local structures may be rearranged based on other criteria, such as based on the identifiers, based on the classification of the sites, body tissues or viscera, based on the purpose of the study, based on the details of the treatment, or based on the possibility of metastasis or a complication. Alternatively, the local structures may be rearranged based on the distance or direction from an anatomical position or the like in response to the sort button G1 provided in the position information being pressed down.

Figure 14:
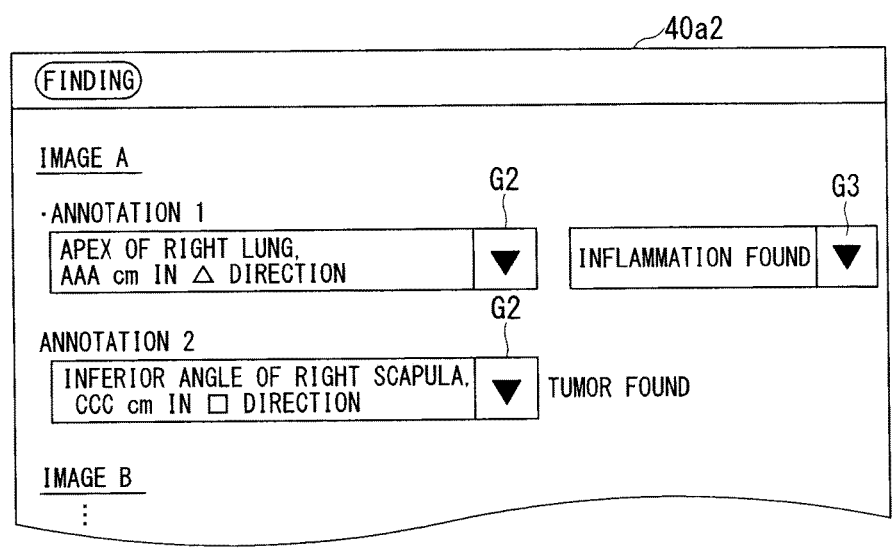
FIG. 14 is a diagram for illustrating another example of how the key image local structure list is displayed in the image interpretation report creating apparatus 100 according to the first embodiment.

FIG. 14 is a diagram for illustrating another example of how the key image local structure list is displayed in the image interpretation report creating apparatus 100 according to the first embodiment. FIG. 14 shows an example of how the finding entry field is displayed after a local structure is selected from the key image local structure list. FIG. 14 show an example in which two annotations are set for one attached key image. A description "APEX OF RIGHT LUNG, INFLAMMATION found at AAA cm in Δ direction" is shown for an annotation 1. The description "APEX OF RIGHT LUNG, at AAA cm in Δ direction" is automatically displayed when the local structure is selected from the key image local structure list. Similarly, a description "INFERIOR ANGLE OF RIGHT SCAPULA, TUMOR found at CCC cm in □ direction" is shown for an annotation 2. In this way, information that indicates the anatomical position "INFERIOR ANGLE OF RIGHT SCAPULA, at CCC cm in □ direction" is automatically displayed, and the user, such as a reader, has only to enter only a symptom observed at the anatomical site.

In addition, each attached key image or annotation and the text shown in the finding are associated with each other, and the text can be associated with the coordinates of the attached key image or annotation even if the text is explicitly shown as a character string in the finding.

In addition, even if a plurality of key images are selected at the same time and moved into the key image attachment region, the key image local structure list can be displayed for each of the attached key images. With such a function, selection of an attached key image does not have to be performed each time a finding is entered.

Furthermore, as shown by a button G3, a symptom or the like associated with the local structure can also be automatically input simply by selecting a boilerplate text in a pull-down menu or the like. For example, a list of boilerplate texts associated with the local structure selected from the key image local structure list can be generated and displayed in the same format as the key image local structure list shown in FIGS. 12 and 14. Alternatively, the list of boilerplate texts may be created based on the study information, including the purpose of the inspection, or the patient information, including the anamnesis.

A local structure once selected can be changed by pressing down a pull-down menu button "G2" shown in FIG. 14. When the pull-down menu button G2 is pressed down, the key image local structure list is displayed again, and a local structure can be selected again. If the pull-down menu includes an option of "addition", "deletion", "change" or the like, the number of local structures used in the finding can be increased or decreased.

As described above, according to the first embodiment, the task of collecting information required to describe the anatomical position to be mentioned in the finding is not required. According to the first embodiment, local structures that are considered to be involved in the finding are identified based on the attached key image displayed in a list format, so that the user does not have to manually enter the local structures. With such a function, common local structures are used to describe positions at which findings are observed in all the created image interpretation reports, so that information sharing among readers or responsible doctors can be facilitated.

Second Embodiment

Figure 15:
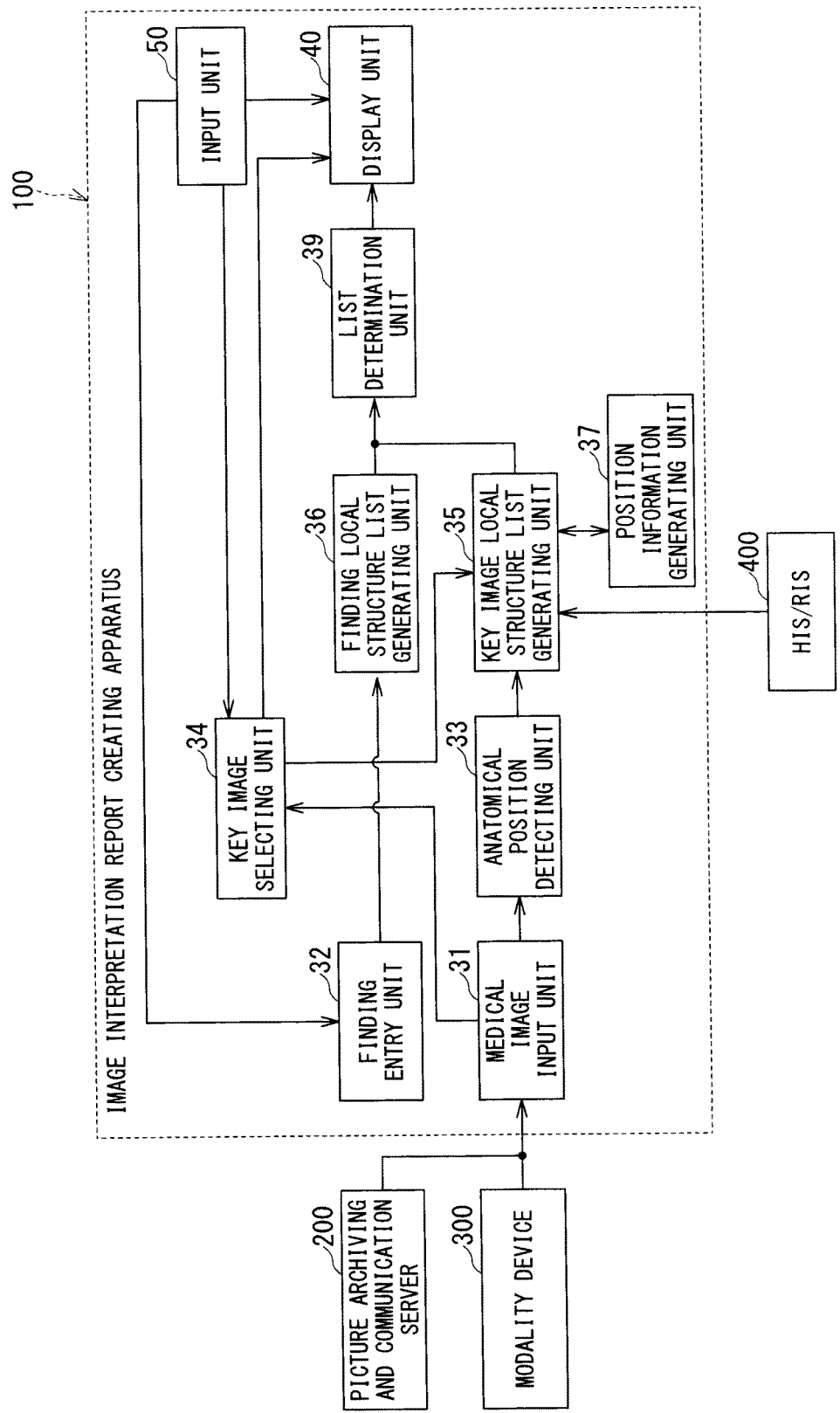
FIG. 15 is a functional block diagram showing an example of a functional configuration of the image interpretation report creating apparatus 100 according to the second embodiment.

The second embodiment relates to an operation that occurs when a key image is selected after a finding is entered.
(1) Configuration
FIG. 15 is a functional block diagram showing an example of a functional configuration of the image interpretation report creating apparatus 100 according to the second embodiment. The same components as those in the first embodiment shown in FIG. 2 are denoted by the same reference numerals, and redundant description thereof will be omitted.

As shown in FIG. 15, in addition to the components of the functional configuration according to the first embodiment, the image interpretation report creating apparatus 100 comprises a finding entry unit 32, a finding local structure list generating unit 36 serving as a second local structure information generating unit, and a list determination unit 39. The functions of the finding entry unit 32, the finding local structure list generating unit 36 and the list determination unit 39 are implemented by the main control unit 30 executing a program stored in the storage unit 20.

The finding entry unit 32 obtains a finding input through the input unit 50. The finding includes at least a status of a predetermined site (a symptom, a status of an abnormality or the like) and a description of the position in the predetermined site at which the symptom or the abnormality is observed. The position included in the finding is represented by the name of the local structure, the site, the viscus or the like or the direction or distance therefrom. Information input to the finding entry unit 32 will be referred to as finding information, hereinafter.

The finding local structure list generating unit 36 serving as a second local structure information generating unit identifies a local structure relating to the predetermined site included in the finding information input to the finding entry unit 32. The finding local structure list generating unit 36 then generates information on the identified local structure as second local structure information and makes the display unit 40 display the information. In the following description, an example will be described in which the second local structure information is information on local structures in a list format (referred to as a finding local structure list, hereinafter) will be described. The finding local structure list is a list of not only local structures relating to the finding information but also local structures located in a vicinity of the local structures and local structures extracted based on the site, the viscus or the like described in the inspection request. That is, the finding local structure list is a list of local structures created based on the finding information. The finding local structure list generated by the finding local structure list generating unit 36 will be further described later.

The key image selecting unit 34 provides the information on the image (key image) selected after entry of the finding to the list determination unit 39. As in the first embodiment, it is essential only that the key image is selected from among a plurality of sub-images forming the medical image by the key image selecting unit 34 and associated with a new image interpretation report currently being created, and the key image may not be attached to the image interpretation report.

Upon receiving the information on the key image selected after entry of the finding, the list determination unit 39 determines whether the local structure included in the key image local structure list is included in the finding local structure list or the like. In the following, an example will be described in which the list determination unit 39 determines whether the local structure included in the key image local structure list is included in the finding local structure list or not when the key image is attached to the image interpretation report, that is, in the case where the key image is an attached key image. If the key image local structure list created for the attached key image includes no local structure included in the finding local structure list created based on the finding information, the list determination unit 39 determines that the image is not a key image relating to the input finding, and notifies the user of the result of the determination. A determination method performed by the list determination unit 39 will be described later.

(2) Operation

Figure 16:
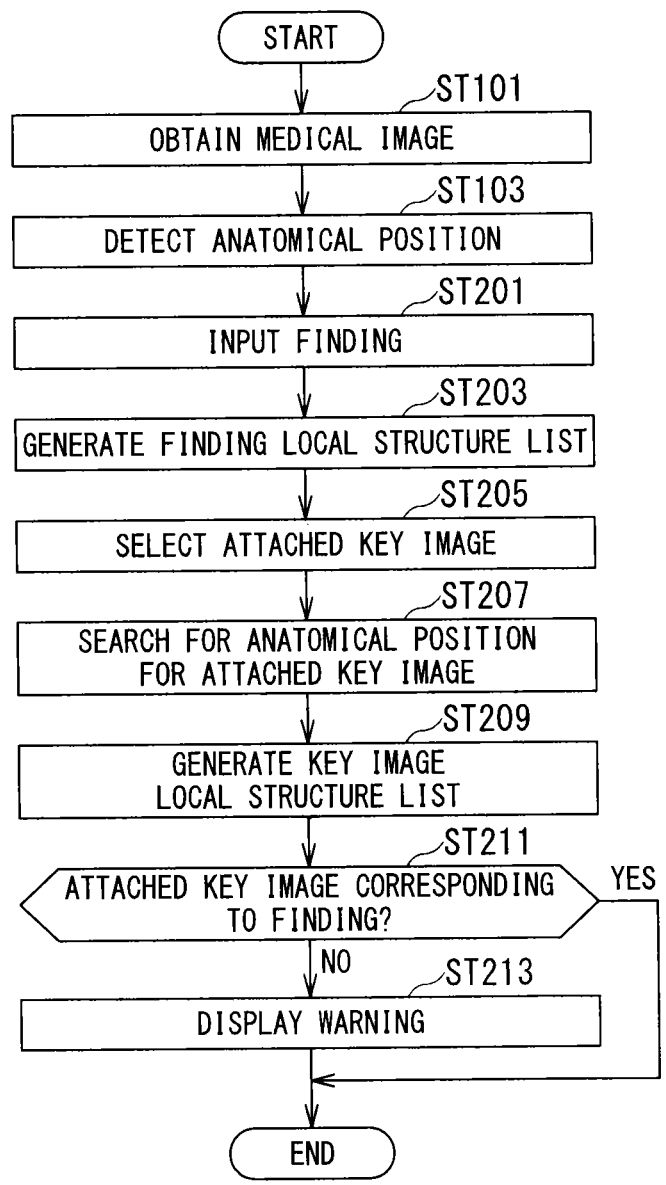
FIG. 16 is a flowchart showing an example of an operation of the image interpretation report creating apparatus 100 according to the second embodiment.

FIG. 16 is a flowchart showing an example of an operation of the image interpretation report creating apparatus 100 according to the second embodiment. The same processings as those in the first embodiment described above with reference to FIG. 3 are denoted by the same reference numerals, and redundant description thereof will be omitted.

In ST201, finding information is input through the input unit 50.

In ST203, the finding local structure list generating unit 36 generates a finding local structure list based on the finding information.

In ST205, the key image selecting unit 34 selects an attached key image from among key images selected from among a plurality of medical images included in the medical image data in response to an input through the input unit 50. It is essential only that the key image is selected from among a plurality of sub-images forming the medical image by the key image selecting unit 34 and associated with a new image interpretation report currently being created, and the key image may not be attached to the image interpretation report. In the following, an example will be described in which the key image selecting unit 34 provides information on the key image (attached key image) to the key image local structure list generating unit 35 and the list determination unit 39 when the key image is attached to the image interpretation report, that is, in the case where the key image is an attached key image.

In ST207, the key image local structure list generating unit 35 retrieves an anatomical position for the attached key image.

In ST209, the key image local structure list generating unit 35 generates a key image local structure list based on the retrieved anatomical position for the attached key image.

In ST211, the list determination unit 39 determines whether the key image local structure list includes a local structure included in the finding local structure list or not. If the key image local structure list includes a local structure included in the finding local structure list, the list determination unit 39 determines that the attached key image is an attached key image relating to the finding. On the other hand, if the key image local structure list includes no local structure included in the finding local structure list, the list determination unit 39 determines that the attached key image is not an attached key image relating to the finding and notifies the user of the result of the determination by displaying a warning message or the like (ST213).

Figures 17A, 17B, 17C:
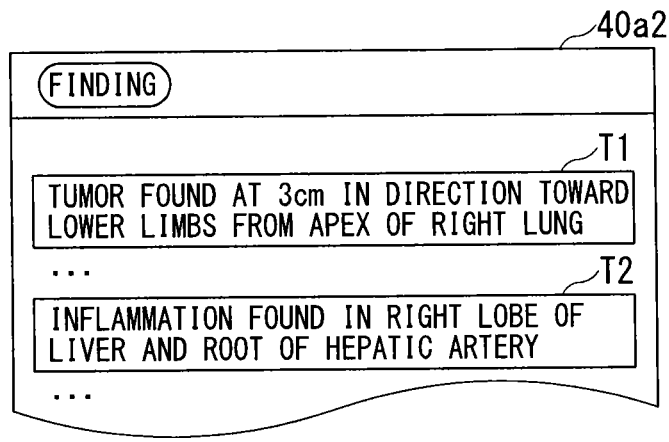
FIG. 17A shows an example of findings according to the second embodiment.
FIG. 17B shows an example of a finding local structure list created from the finding display region T1 shown in FIG. 17A.
FIG. 17C shows an example of a finding local structure list created from the finding display region T2 shown in FIG. 17A.

FIG. 17 are diagrams for illustrating findings with regard to the image interpretation report creating apparatus 100 according to the second embodiment. A finding entry field 40a2 shown in FIG. 17A is the same as the finding entry field 40a2 shown in FIG. 7 or other drawings. In the finding entry field 40a2 shown in FIG. 17A, a position at which the finding is observed, such as a local structure, the name of a viscus, the name of a site or the like that corresponds to the finding, is entered through the input unit 50 provided with a keyboard, a mouse or the like. For example, the finding is described with a text such as "TUMOR FOUND AT 3 CM IN DIRECTION TOWARD LOWER LIMBS FROM APEX OF RIGHT LUNG" shown in a finding display region T1 in FIG. 17A, or with a symptom or abnormality observed at a plurality of positions such as "INFLAMMATION FOUND IN RIGHT LOBE OF LIVER AND ROOT OF HEPATIC ARTERY" shown in a finding display region T2.

FIGS. 17B and 17C show examples of the finding local structure list generated by the finding local structure list generating unit 36. The finding local structure list generating unit 36 analyzes a character string entered in the finding and generates the finding local structure list such as those shown in FIGS. 17B and 17C.

The table shown in FIG. 17B is a finding local structure list created from the finding display region T1 shown in FIG. 17A. From the finding display region T1 shown in FIG. 17A, texts "APEX OF RIGHT LUNG" and "3 CM IN DIRECTION TOWARD LOWER LIMBS" can be obtained as texts that indicate an anatomical position. The "APEX OF RIGHT LUNG" is a text that describes a local structure and therefore extracted as a local structure that corresponds to the finding. In addition, a local structure that exists at a distance of "3 CM IN DIRECTION TOWARD LOWER LIMBS" from the apex of the right lung may be extracted and added to the list.

The table shown in FIG. 17C is a finding local structure list created from the finding display region T2 shown in FIG. 17A. From the finding display region T2 shown in FIG. 17A, texts "RIGHT LOBE OF LIVER" and "ROOT OF HEPATIC ARTERY" can be obtained. The "RIGHT LOBE OF LIVER" is the name of the viscus or a part of the viscus, and data on local structures is associated with such classification. Using this data, as shown in FIG. 17C, "MOST INFERIOR ASPECT OF LIVER" and "POSTERIOR ASPECT OF LIVER" are extracted as local structures that correspond to the "RIGHT LOBE OF LIVER". In addition, based on the text "RIGHT LOBE OF LIVER", local structures relating to the liver may be extracted as a finding local structure list. In the finding in the finding display region T2 in FIG. 17A, the text "ROOT OF HEPATIC ARTERY" is also included to indicate an anatomical position. A local structure "ORIGIN OF HEPATIC ARTERY" may be extracted by prefix search, or a character string "ORIGIN" may be estimated from the character string "ROOT" in the text.

Although texts close to the names of local structures are used in the examples shown in FIG. 17, different readers uses different expressions to describe anatomical sites, such as "an upper right part of a lung", "a part of the right lung", "a right position in the liver", "an upward direction" or "a lower part". The finding local structure list generating unit 36 has a search function ready for such different expressions or a narrow-down function relying on the study information, or has a database of correspondences between input texts and local structures stored in the storage unit 20 or an external storage device to identify the local structure relating to the input finding.

As described above, the finding local structure list is a list of local structures relating to a site or viscus corresponding to a character string included in the entered finding.

Figure 18:
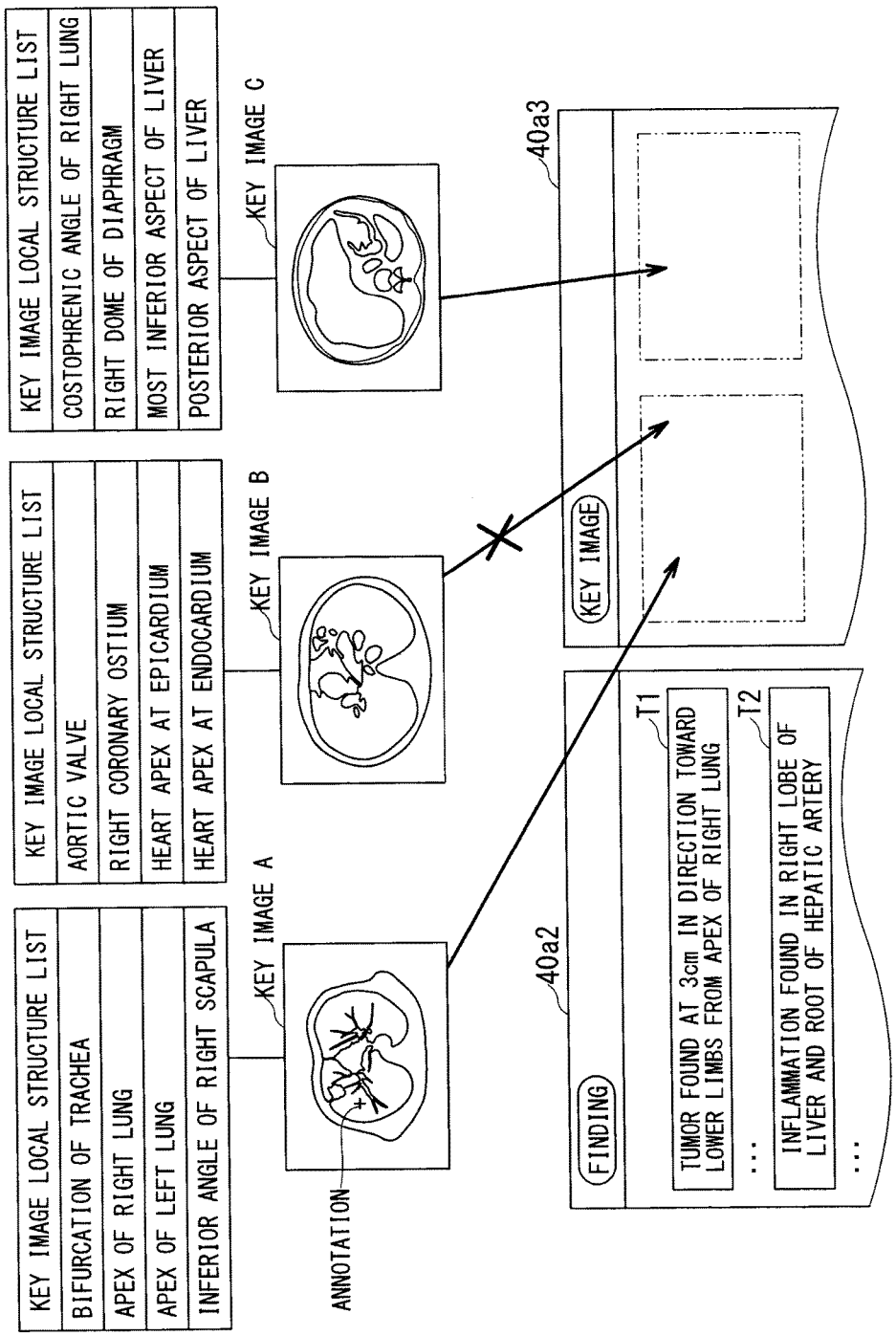
FIG. 18 is a diagram for illustrating determination of a key image in the image interpretation report creating apparatus 100 according to the second embodiment.

FIG. 18 is a diagram for illustrating determination of a key image in the image interpretation report creating apparatus 100 according to the second embodiment. In the upper part of FIG. 18, key images and key image local structure lists corresponding to the key images are shown. The key image local structure list corresponding to a left-hand key image A in the upper part of FIG. 18 includes "BIFURCATION OF TRACHEA", "APEX OF RIGHT LUNG", "APEX OF LEFT LUNG" and "INFERIOR ANGLE OF RIGHT SCAPULA". If the key image A is moved into the key image attachment region 40a3 as an attached key image, three local structures "BIFURCATION OF TRACHEA", "APEX OF RIGHT LUNG" and "INFERIOR ANGLE OF RIGHT SCAPULA" match with the local structures included in the finding local structure list. Since the local structures in the key image local structure list are included in the finding local structure list, the list determination unit 39 determines that the key image A is a key image relating to the finding.

Similarly, the key image local structure list corresponding to a right-hand key image C in the upper part of FIG. 18 includes "COSTOPHRENIC ANGLE OF RIGHT LUNG", "RIGHT DOME OF DIAPHRAGM", "MOST INFERIOR ASPECT OF LIVER" and "POSTERIOR ASPECT OF LIVER". If the key image C is moved into the key image attachment region 40a3, two local structures "MOST INFERIOR ASPECT OF LIVER" and "POSTERIOR ASPECT OF LIVER" match with the local structures included in the finding local structure list. Since the local structures in the key image local structure list are included in the finding local structure list, the list determination unit 39 determines that the key image C is also a key image relating to the finding.

The list of image landmarks corresponding to a center key image B in the upper part of FIG. 18 includes "AORTIC VALVE", "RIGHT CORONARY OSTIUM", "HEART APEX AT EPICARDIUM" and "HEART APEX AT ENDOCARDIUM". However, the finding local structure lists shown in FIGS. 17B and 17C do not include any local structure that matches with these local structures. Since no local structure in the key image local structure list is included in the finding local structure list, the list determination unit 39 determines that the key image B is not a key image relating to the finding.

If the list determination unit 39 determines that an attached key image is not a key image relating to the finding, the display unit 40 generates and displays a warning message.

The list determination unit 39 may determine whether one or more key images corresponding to an anatomical site included in the finding are attached or not. If creation of the image interpretation report is to be finished when no key image corresponding to the finding has been attached, a warning message can be displayed to prevent attachment of a key image from being omitted. Furthermore, the list determination unit 39 can also check whether any finding corresponding to a local structure in a key image attached to the image interpretation report has been entered or not, thereby preventing entry of a finding from being omitted. Furthermore, the list determination unit 39 may narrow down likely slice images as key images in the medical image data in advance based on the finding local structure list generated based on the finding.

As described above, the image interpretation report creating apparatus 100 according to the second embodiment can prevent a key image that does not relate to the finding included in the image interpretation report from being associated with (attached to, for example) the image interpretation report using the finding information. In addition, the image interpretation report creating apparatus 100 can check whether a key image relating to the finding is associated with the image interpretation report or not (attached to the image interpretation report or not, for example), thereby preventing association of a key image (attachment of a key image, for example) from being omitted.

Third Embodiment

Figure 19:
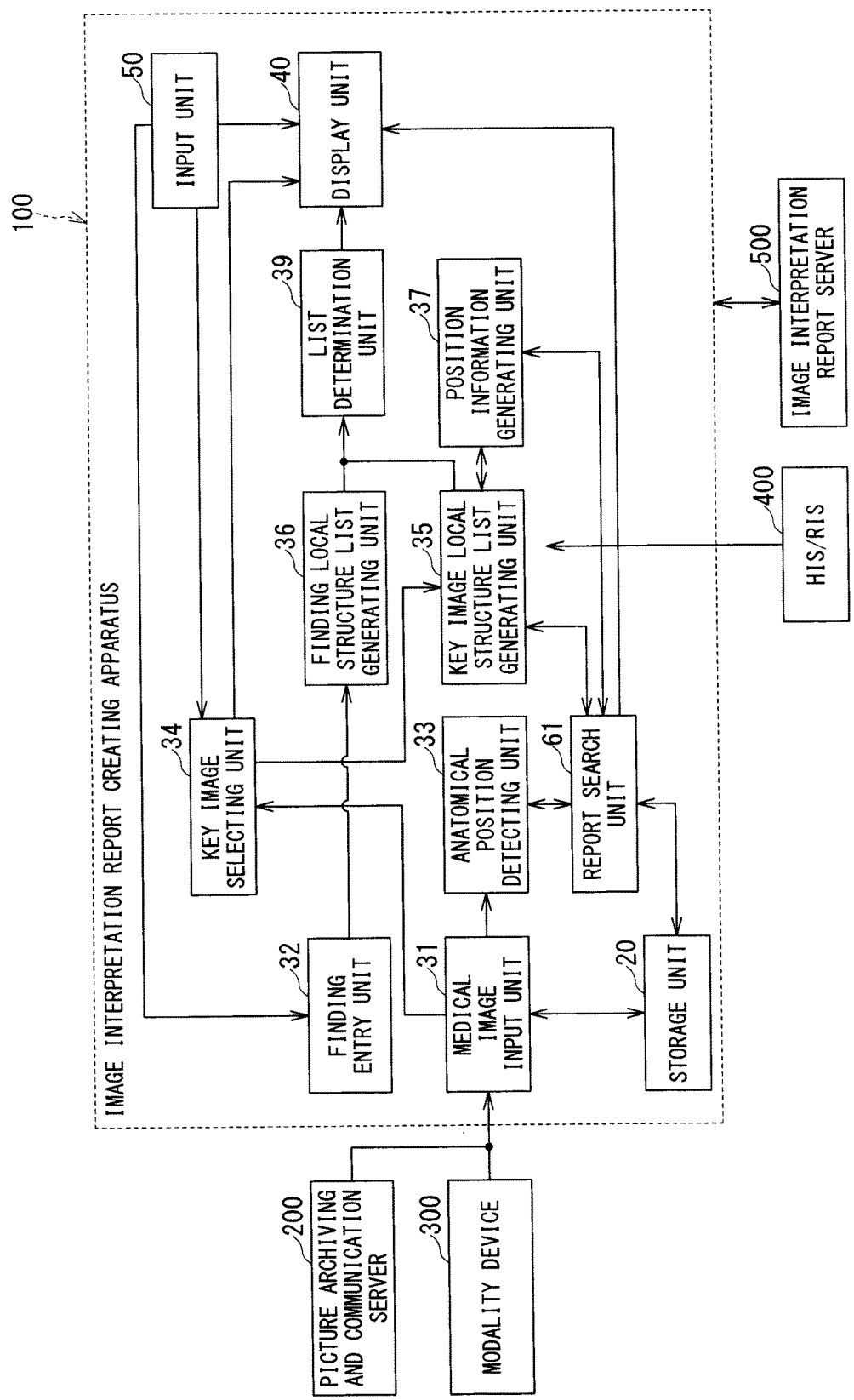
FIG. 19 is a functional block diagram showing an example of a functional configuration of the image interpretation report creating apparatus 100 according to a third embodiment.

FIG. 19 is a functional block diagram showing an example of a functional configuration of the image interpretation report creating apparatus 100 according to a third embodiment.

The image interpretation report creating apparatus 100 according to the third embodiment differs from the image interpretation report creating apparatuses 100 according to the first and second embodiments in that, when creating a new image interpretation report, the image interpretation report creating apparatus 100 is configured to present, to the user as a reference image interpretation report, another image interpretation that is expected to be helpful. In other respects, the image interpretation report creating apparatus 100 is substantially the same as the image interpretation report creating apparatus according to the first embodiment shown in FIG. 2, and redundant description of the common parts will be omitted.

In general, when a part image interpretation report to be referred to is searched for based on limited information such as the type of the modality device or the name of the patient, a vast number of image interpretation reports can be output as the search result. In such a case, the reader or the like inconveniently has to manually search for a helpful image interpretation report by checking the contents of the vast number of image interpretation reports for matching of details of inspections for which reports are created or imaged anatomical positions or sites.

In view of such a circumstance, the image interpretation report creating apparatus 100 according to the third embodiment has a capability of readily presenting, to the user, an image interpretation report to be referred to based on the position of a local structure, in addition to the capabilities of the image interpretation report creating apparatuses 100 according to the first and/or second embodiments.

The image interpretation report creating apparatus 100 according to this embodiment is connected to an image interpretation report server 500 as well as the picture archiving and communication server 200, the modality device 300 and the HIS/RIS 400 via the communication controlling device 10 and the electronic network. In this case, the picture archiving and communication server 200, the HIS/RIS 400, the image interpretation report server 500 and the image interpretation report creating apparatus 100 may be configured as a cloud image interpretation report creating system.

The image interpretation report server 500 stores an image interpretation report created by a reader or the like. The image interpretation report is associated with an inspection request, a finding, a medical image and a key image selected from among a plurality of sub-images forming the medical image. Information on the inspection request, the finding, the medical image and the key image may be retained in the image interpretation report server 500 as a whole or retained in association with data accumulated in the HIS/RIS 400 or the picture archiving and communication server 200 based on an ID that uniquely identifies the inspection request or medical image.

As shown in FIG. 19, the image interpretation report creating apparatus 100 according to the third embodiment comprises a report search unit 61, the storage unit 20, the display unit 40 and the input unit 50. The report search unit 61 is implemented by the processor of the main control unit 30 executing a program stored in the storage unit 20, for example.

The storage unit 20 stores medical image data received from the picture archiving and communication server 200 or the modality device 300 via the medical image input unit 31. The storage unit 20 also stores medical image data for which a new image interpretation report to be created and medical image data associated with a reference report to be referred to when the new image interpretation report is created. The medical image data stored in the storage unit 20 or the picture archiving and communication server 200 is provided to the medical image input unit 31.

The storage unit 20 further stores a plurality of image interpretation reports associated with a key image. In the following description, a new image interpretation report currently being created will be referred to as a "new report", and medical image data for which the new image interpretation report is to be created will be referred to as "new image data". Furthermore, in the following description, an image interpretation report referred to when a new image interpretation report is created will be referred to as a "reference report", and medical image data associated with the reference report will be referred to as "reference image data".

The image interpretation report creating apparatus 100 can create an image interpretation report including a finding with which a key image is associated in the same procedure as described above with reference to the first and second embodiments. The image interpretation report includes at least finding information input to the finding entry unit 32. The finding includes information on the state of a predetermined site (an abnormality found by image interpretation, for example). For example, in the finding, the anatomical position or site at which the abnormality is observed, and the status of the abnormality are recorded. In the following, an example will be described in which the image interpretation report includes a finding, and a key image selected by the key image selecting unit 34 is attached to the image interpretation report. The image interpretation report created by the image interpretation report creating apparatus 100 is stored in the storage unit 20 and the image interpretation report server 500.

To the medical image data (reference image data) associated with the reference report and stored in the storage unit 20, anatomical position information is attached. For example, the anatomical position detecting unit 33 attaches anatomical position information to a medical image (including a key image) associated with an image interpretation report created by the image interpretation report creating apparatus 100.

In creation of a new report, based on the key image local structure information for the new report, the report search unit 61 searches the storage unit 20 for an image interpretation report (reference report) that resembles the new report and will be helpful in creating the new report and makes the display unit 40 display the image interpretation report.

If a vast number of reference reports are found, the report search unit 61 can narrow down the reference reports based on a criterion specified by the user through the input unit 50.

For example, the specified criterion can be the "degree of matching" between the new report and the reference report. The degree of matching referred to herein means the similarity between the new report and another image interpretation report expressed numerically. When the degree of matching is used for narrowing down the reference reports, the reference reports can be narrowed down based on whether or not the degree of matching for each reference report is equal to or greater than a threshold specified by the user through the input unit 50, and the display unit 40 can display the narrowed-down reference reports.

The degree of matching between the new report and each of a plurality of image interpretation reports can be determined based on the key image local structure list for each of the plurality of image interpretation reports stored in the storage unit 20 and key image local structure information in the new report. And an image interpretation report for which the degree of matching is equal to or greater than a predetermined value is selected from among the plurality of image interpretation reports stored in the storage unit 20, and the display unit 40 displays the image interpretation report.

The key image local structure list for the new report is generated by the key image local structure list generating unit 35 based on the key image selected and associated with the new report by the key image selecting unit 34 as described above with reference to the first and second embodiments. The key image local structure list for each of the plurality of image interpretation reports stored in the storage unit 20 is generated by the key image local structure list generating unit 35 based on the key image associated with the image interpretation report.

The report search unit 61 can also determine the degree of matching based on information such as the kind of the site or the percentage of the site. In that case, the degree of matching determined by the report search unit 61 increases with the degree of matching between the site of the local structure included in the key image local structure list for the image interpretation report stored in the storage unit 20 and the site specified by the user through the input unit 50 or with the degree of matching between the site of the local structure included in the key image local structure list for the image interpretation report stored in the storage unit 20 and the site of the local structure included in the key image local structure list for the new report.

If a key image is identified for the new image and the reference image, the report search unit 61 can also calculate the degree of matching based on the key image. In that case, the degree of matching can be calculated based on whether or not the new report and the reference report match with each other with regard to the local structure (closest AL) that corresponds to the anatomical position closest to the key image or based on the type or percentage of the closest AL. If there are a plurality of key images, a representative key image can be extracted for calculation of the degree of matching. Alternatively, the degree of matching may be calculated based on the distance from the anatomical position of the closest AL to a predetermined position in the key image (closest AL distance). The closest AL distance is calculated by the position information generating unit 37.

The report search unit 61 may identify a predetermined local structure (local structure relating to a site in which metastasis or a complication is expected to occur) from the viewpoint of metastasis or a complication based on the local structures included in the key image local structure list for the new report, search the plurality of image interpretation report stored in the storage unit 20 for an image interpretation report associated with the predetermined local structure, and make the display unit 40 display the image interpretation report as a reference report.

Specifically, the report search unit 61 searches for a reference report associated with a metastasis destination or a complication site based on the local structure associated with a primary site for the new image (referred to as a primary site AL, hereinafter). In this process, a slice image including an anatomical position associated with the metastasis destination/complication site may be displayed from the new image data based on the primary site AL for the new image data, or data relating to an anatomical position relating to the metastasis destination/complication site may be displayed from the primary site AL or new image data based on past study data for the object.

The local structure relating to a site in which metastasis or a complication is expected to occur can be associated with the "primary site AL" and the "disease name" in advance.

Therefore, the report search unit 61 can extract a reference report for a site in which metastasis or a complication is expected to occur with some or all of the local structures in the key image local structure list for the new report being specified as primary site ALs. Furthermore, if the report search unit 61 obtains an assumed disease name or a disease name in the anamnesis or the like from the inspection request or the like associated with the new report, the report search unit 61 can narrow down the reference reports based on not only the primary site ALs but also the disease name. If the reference report including a local structure in which metastasis or a complication can occur is checked based on the key image local structure list for the new report, metastasis or a complication can be prevented from being missed.

Alternatively, the report search unit 61 may search the plurality of image interpretation reports stored in the storage unit 20 for an image interpretation report interpreted in an image interpretation procedure similar to the image interpretation procedure for the new report, and make the display unit 40 display the image interpretation report. More specifically, the report search unit 61 can narrow down the reference reports based on the similarity of various processes or procedures performed in image interpretation, such as the type of the navigation of the image interpretation procedure used in image interpretation, the order of image interpretation, or the type of the image processing used for image interpretation.

FIG. 20 is a diagram for illustrating a first example of a screen for inputting a narrow-down criterion of the image interpretation report creating apparatus 100 according to the third embodiment.

The report search unit 61 generates a reference report list T3, which is a list of reference reports, and makes the display unit 40 display the reference report list T3. The user can rearrange the rows in the reference report list T3 by pressing down a button B1 in FIG. 20. For example, if an upper button B1 is pressed down, the rows are rearranged in ascending order of the date of report creation. And if a lower button B1 is pressed down, the rows are rearranged in descending order of the date of report creation.

Alternatively, a list of data in the rows may be displayed when the button B1 is pressed down. A table T4 is an example of how the list of data in the rows is displayed when the button B1 at the representative site in the reference report list T3 is pressed down. In the example shown in FIG. 20, the table T4 includes "HEAD", "CHEST" and "ABDOMEN", and the reference reports are narrowed down based on the kinds of the representative sites by selecting one or more sites by checking the corresponding checkboxes.

Alternatively, as shown in FIG. 20, a narrow-down criterion may be input through a pull-down menu (see a narrow-down criterion 1 in FIG. 20). FIG. 20 shows an example in which "METASTASIS DESTINATION/COMPLICATION SITE" is selected as a narrow-down criterion. If the "METASTASIS DESTINATION/COMPLICATION SITE" is selected, the report search unit 61 selectively extracts the reference reports relating to the metastasis destination/complication site based on the primary site Al for the new image and makes the display unit 40 display the reference reports.

Although FIG. 20 shows an example in which "METASTASIS DESTINATION/COMPLICATION SITE" is selected in the pull-down menu as a narrow-down criterion, the reference reports can also be narrowed down based on the similarity of various processes or procedures performed in image interpretation, such as the type of the navigation of the image interpretation procedure used in image interpretation, the order of image interpretation, or the type of the image processing used for image interpretation. In addition, a slice image including an anatomical position associated with the metastasis destination/complication site may be displayed from the new image data based on the primary site AL for the new image data, or data relating to an anatomical position relating to the metastasis destination/complication site may be displayed from the primary site AL or new image data based on past study data for the object.

FIG. 21 is a diagram for illustrating a second example of the screen for inputting a narrow-down criterion of the image interpretation report creating apparatus 100 according to the third embodiment. FIG. 21 shows an example in which a degree-of-matching calculation criterion is used as a narrow-down criterion.

As shown in a degree-of-matching calculation criterion accepting window W1 in FIG. 21, the user can input a target of degree-of-matching calculation and a calculation method as narrow-down criteria. In that case, the calculation criterion input through the input unit 50 is input to the report search unit 61. The report search unit 61 determines the degree of matching in accordance with the input criterion. The user can press down the button B2 to display a pull-down menu of degree-of-matching calculation criteria. FIG. 21 shows an example in which "CLOSEST AL FOR KEY IMAGE" is selected as a criterion 1, "DISTANCE" is selected as a criterion 2, and the pull-down menu includes options PRESENCE OR ABSENCE OF MATCHING, NUMBER OF MATCHINGS and PERCENTAGE OF MATCHING in addition to the "DISTANCE". Furthermore, another criterion (another calculation criterion or a weighting criterion, for example) can also be added by pressing a button B3. The calculation criterion can be changed again and again. The report search unit 61 may calculate the degree of matching each time the calculation criterion is changed, or a degree-of-matching calculation button or the like may be provided in the screen, and the degree-of-matching calculation may be performed each time the button is pressed down.

Furthermore, as shown in FIG. 21, in the degree-of-matching calculation criterion accepting window W1, a field for entry of a narrow-down criterion for the numerical value of the degree of matching may be provided. FIG. 21 shows an example in which "0.8" is entered in an input box for a narrow-down criterion for the numerical value of the degree of matching, and a radio button "equal to or greater than" displayed at a side of the input box is selected, so that the narrow-down criterion for the numerical value of the degree of matching is specified as "equal to or greater than 0.8".

In this way, the reference reports can be narrowed down depending on the numerical value of the degree of matching by setting the narrow-down criterion for the numerical value of the degree of matching. Furthermore, when the "DISTANCE" is selected as the degree-of-matching calculation criterion, an image T5 for selection of a distance calculation method can be displayed. In that case, since the degree of matching can be calculated by combination of a plurality of distances, a plurality of distance calculation methods may be selected by checking a plurality of checkboxes.

Furthermore, the report search unit 61 may generate, for a thumbnail image of each of the plurality of image interpretation reports stored in the storage unit 20, a superimposed image that is a human body chart representing a human body on which a mapping chart with a mark indicating the position of a local structure included in the key image local structure information for the image interpretation report is superimposed, and make the display unit 40 display the plurality of superimposed images generated.

FIG. 22 is a diagram for illustrating a case of displaying thumbnails of reference reports.

In the example shown in FIG. 22, a reference report selection window W2 is displayed on the display unit 40. When a thumbnail image (icon) is selected from among thumbnail images representing reference reports by the user through the input unit 50, the report search unit 61 makes the display unit 40 display the selected reference report.

A reference report indication D1 shown in the reference report selection window W2 in FIG. 22 is a thumbnail image of the reference report. If there are a plurality of pages of reference report images, the reference report indication D1 can be a thumbnail image of a representative page or the first page. In the thumbnail image of the reference report, a finding included in the reference report or a key image is also shown.

On the reference report indication D1 shown in FIG. 22, a chart representing a human body (human body chart) D2 is superimposed. The human body chart D2 may be a common human body anatomical chart, for example. The following description will be made in the context of using the human body anatomical chart as the human body chart, as an example. The human body anatomical chart is a diagram that represents viscera, sites and organs in the human body by illustrations or pictures to help understanding of the positions, appearances and shapes of structures in the human body. The anatomical chart may be two-dimensional or three-dimensional. The anatomical chart may be prepared for each site, such as the head or the chest, or for each system, such as the heart, the liver, the respiratory system or the digestive system. The anatomical chart may be prepared for any of the coronal plane, the sagittal plane and the transverse plane. For example, a coronary anatomical chart of a human body may be one of a series of two-dimensional anatomical charts taken from the dorsal side to the ventral side or may be an anatomical chart displayed as a predetermined cross section of a three-dimensional anatomical chart. The anatomical chart may be downloaded from an external storage device, or may be referred to in the external storage device.

A dot shown in the anatomical chart D2 indicates the position of the closest AL or annotation in the key image for the reference report. The dot shown in the anatomical chart D2 may be shown at a position corresponding to an anatomical position in the new image.

In the upper part of the reference report selection window W2, pull-down menus for inputting a narrow-down criterion are displayed. The reference reports can be narrowed down not only by using these pull-down menus but also using the anatomical chart that shows an anatomical position in the new image. For example, the display unit 40 can display both an anatomical chart showing an anatomical position in the new image and the reference report selection window W2, and an anatomical position in the new image can be selected to narrow down the reference reports.

In the reference report selection window W2 shown in FIG. 22, an anatomical position relating to a reference report can be displayed on an anatomical chart. Therefore, the user can visually select a reference report. In addition, since the anatomical chart is displayed, the reference reports can be intuitively narrowed down.

Figure 23:
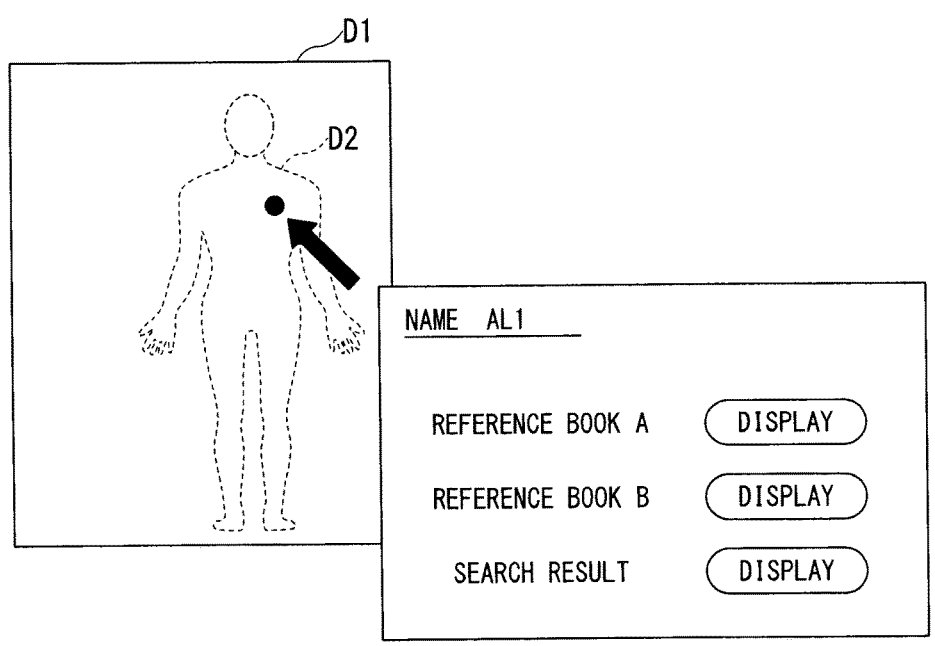
FIG. 23 is a diagram for illustrating an example of a reference information indication on the image interpretation report creating apparatus 100 according to the third embodiment.

FIG. 23 is a diagram for illustrating an example of a reference information indication on the image interpretation report creating apparatus 100 according to the third embodiment. The reference information indication is generated by the report search unit 61 based on the anatomical position.

FIG. 23 shows an icon of a reference report, which is the reference report indication D1 on which the anatomical chart D2 is superimposed shown in FIG. 22. As shown in FIG. 23, by selecting a dot on the anatomical chart D2, a local structure corresponding to the dot, a reference book, a reference literature, medical information, symptom information relating to the local structure, or the result of search of the Internet concerning the local structure can be displayed.

For example, if a dot on the anatomical chart D2 is selected, a pop-up is displayed (see FIG. 23). In the pop-up, a "DISPLAY" button can be pressed down to display a reference book relating to the corresponding local structure and a symptom or the like relating to the local structure, or to display an explanation or the like of the relevant anatomical position or site retrieved from an anatomical dictionary or the like. Such reference books or the like may be stored in the storage unit 20 of the image interpretation report creating apparatus 100, downloaded from an external storage device or referred to in the external storage device. Furthermore, the result of search of the Internet concerning the local structure may be displayed. In this way, the user, such as a reader, can obtain various kinds of information from the image interpretation report creating apparatus 100 by investigating the local structure.

The image interpretation report creating apparatus 100 according to the third embodiment has the same advantages as the image interpretation report creating apparatuses 100 according to the first and second embodiments. In addition, the image interpretation report creating apparatus 100 according to the third embodiment can search, with high precision, for an image interpretation report that will be helpful in creating a new image interpretation report based on an anatomical position in the new image data. In addition, the image interpretation report creating apparatus 100 can also search for a reference report based on an anatomical position in a vicinity of a key image identified in the new image and refer to an image interpretation report that is closer to the new image interpretation report being created in terms of conditions. Therefore, more parts of the reference report can be borrowed into the new report, and the image interpretation report can be more efficiently created. In addition, since the anatomical position is used to search for a reference report relating to metastasis or a complication site, a relevant reference report can be found without fail.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An image interpretation report creating apparatus that creates an image interpretation report that includes a finding and is associated with a key image, comprising:
   processing circuitry configured to
      select a sub-image as the key image from among a plurality of sub-images comprising a medical image,
      extract at least one local structure in a human body from the medical image,
      calculate a position of each extracted local structure, identify a first local structure, the identified first local structure being included in the extracted at least one local structure, within a first predetermined distance from a position of the key image, calculate a distance from a position of the identified first local structure to a coordinate of an annotation in the key image, to a coordinate of a center of the key image, or to a coordinate of a viscus to be inspected in the key image, and generate information on the identified local structure when the calculated distance is shorter than a second predetermined distance, as first local structure information; and a display configured to display the first local structure information as a candidate to be entered in an entry field for the finding.

2. The image interpretation report creating apparatus according to claim 1, wherein the processing circuitry is further configured to:

receive input of at least the finding including a state of a predetermined site concerning the medical image;

identify a second local structure associated with the predetermined site included in the finding and generate information on the identified second local structure as second local structure information; and determine whether the first local structure included in the first local structure information exists in the second local structure information or not, wherein the display displays a result of the determination when the key image is selected.

3. The image interpretation report creating apparatus according to claim 1, wherein each of the plurality of sub-images comprising the medical image is a slice image, a specific number is assigned to each slice image, and the processing circuitry is further configured to use a coordinate of the position of the first local structure or a number of a slice number at the position of the first local structure as an indication of the position of the first local structure.

4. The image interpretation report creating apparatus according to claim 1, wherein the processing circuitry is further configured to rearrange the first local structure information based on the calculated distance.

5. The image interpretation report creating apparatus according to claim 1, wherein the processing circuitry is further configured to narrow down local structures included in the first local structure information based on at least any of information on a site to be inspected, information on a purpose of an inspection, and information on details of a treatment included in an inspection request.

6. The image interpretation report creating apparatus according to claim 1, further comprising:

a memory to store a plurality of image interpretation reports, wherein the processing circuitry is further configured to search the plurality of image interpretation reports stored in the memory for an image interpretation report for reference of a new image interpretation report currently being created based on the first local structure information for the new image interpretation report.

7. The image interpretation report creating apparatus according to claim 6, wherein the processing circuitry is further configured to determine a degree of matching between each of the plurality of image interpretation reports stored in the memory and the new image interpretation report based on the first local structure information for the image interpretation report stored in the memory and the first local structure information for the new image interpretation report, search the plurality of image interpretation reports stored in the memory for an image interpretation report for which the degree of matching is equal to or greater than a predetermined value, and make the display display the image interpretation report, the first local structure information for the new image interpretation report is the first local structure information generated by the processing circuitry based on a key image selected and associated with the new image interpretation report, and the first local structure information for each of the plurality of image interpretation reports stored in the memory is the first local structure information generated by the processing circuitry based on a key image associated with the each of the plurality of image interpretation reports.

8. The image interpretation report creating apparatus according to claim 6, wherein the processing circuitry is further configured to identify a predetermined local structure from a viewpoint of metastasis or a complication based on the first local structure included in the first local structure information for the new image interpretation report, search the plurality of image interpretation reports stored in the memory for an image interpretation report associated with the predetermined local structure, and make the display display the image interpretation report.

9. The image interpretation report creating apparatus according to claim 6, wherein the processing circuitry is further configured to search the plurality of image interpretation reports stored in the memory for an image interpretation report interpreted in an image interpretation procedure similar to an image interpretation procedure for the new image interpretation report, and make the display display the new image interpretation report.

10. The image interpretation report creating apparatus according to claim 6, wherein the processing circuitry is further configured to generate, for a thumbnail image of each of the plurality of image interpretation reports stored in the memory, a superimposed image that is a human body chart representing a human body on which a mapping chart with a mark indicating a position of a local structure included in the first local structure for each of the plurality of image interpretation reports is superimposed, and make the display display a list of the plurality of generated superimposed images.

11. The image interpretation report creating apparatus according to claim 6, wherein the processing circuitry is further configured to generate an image that represents a reference book, a reference literature, medical information, or symptom information relating to the first local structure, and make the display display the image.

12. The image interpretation report creating apparatus according to claim 1, wherein the processing circuitry is further configured to calculate, when the annotation in the key image has a region, the distance from the position of the first local structure listed in the first local structure information to a coordinate of a center of the annotation in the key image.

13. The image interpretation report creating apparatus according to claim 1, wherein the processing circuitry is further configured to cause the display to display the first local structure information along with the calculated distance.

14. The image interpretation report creating apparatus according to claim 13, wherein the processing circuitry is further configured to calculate the distance and a direction from the position of the first local structure listed in the first local structure information to the coordinate of the annotation in the key image, to the coordinate of the center of the key image, or to the coordinate of the viscus to be inspected in the key image; and cause the display to display the first local structure information along with the calculated distance and direction.

15. A image interpretation report creating system that obtains a medical image of an object through a network and creates a image interpretation report that includes a finding and is associated with a key image, the system comprising:

processing circuitry configured to select a sub-image as the key image from among a plurality of sub-images comprising a medical image, extract at least one local structure in a human body from the medical image, calculate a position of each extracted local structure, identify a first local structure, the identified first local structure being included in the extracted at least one local structure, within a first predetermined distance from an anatomical position corresponding to the key image, calculate a distance from a position of the identified first local structure to a coordinate of an annotation in the key image, to a coordinate of a center of the key image, or to a coordinate of a viscus to be inspected in the key image, and generate information on the identified first local structure when the calculated distance is shorter than a second predetermined distance; and a display configured to display the information on the identified first local structure when the calculated distance is shorter than a second predetermined distance as a candidate to be entered in an entry field for the finding.

* * * * *